US012806147B2

(12) United States Patent
Honjo et al.

(10) Patent No.: US 12,806,147 B2
(45) Date of Patent: Nov. 24, 2026

(54) TIMED-ELUTION MASKING PARTICLES AND ORAL PHARMACEUTICAL COMPOSITION CONTAINING THE SAME

(71) Applicant: TOWA PHARMACEUTICAL CO., LTD., Osaka (JP)

(72) Inventors: Tatsuya Honjo, Osaka (JP); Yusuke Ichibayashi, Osaka (JP); Mitsunori Nishikawa, Osaka (JP); Megumi Murahashi, Osaka (JP); Isamu Saeki, Osaka (JP); Yutaka Okuda, Osaka (JP); Takuya Matsui, Osaka (JP)

(73) Assignee: TOWA PHARMACEUTICAL CO., LTD., Osaka (JP)

( * ) Notice: Subject to any disclaimer, the term of this patent is extended or adjusted under 35 U.S.C. 154(b) by 559 days.

(21) Appl. No.: 18/265,042

(22) PCT Filed: Dec. 4, 2021

(86) PCT No.: PCT/JP2021/044592

§ 371 (c)(1),
(2) Date: Jun. 2, 2023

(87) PCT Pub. No.: WO2022/124243

PCT Pub. Date: Jun. 16, 2022

(65) Prior Publication Data

US 2024/0016745 A1 Jan. 18, 2024

(30) Foreign Application Priority Data

Dec. 8, 2020 (JP) ................................ 2020-203797

(51) Int. Cl.

| | |
|---|---|
| ***A61K 9/20*** | (2006.01) |
| ***A61K 47/02*** | (2006.01) |
| ***A61K 47/34*** | (2017.01) |
| ***A61K 47/38*** | (2006.01) |

(52) U.S. Cl.

CPC ............ *A61K 9/2081* (2013.01); *A61K 47/02* (2013.01); *A61K 47/34* (2013.01); *A61K 47/38* (2013.01)

(58) Field of Classification Search

CPC ...... A61K 9/2081; A61K 47/02; A61K 47/34; A61K 47/38

See application file for complete search history.

(56) References Cited

U.S. PATENT DOCUMENTS

| | | | | |
|---|---|---|---|---|
| 4,844,905 | A | 7/1989 | Ichikawa et al. | |
| 12,090,233 | B2 * | 9/2024 | Honjo | A61K 9/2081 |
| 2005/0287211 | A1 | 12/2005 | Yoshida et al. | |
| 2019/0125666 | A1 | 5/2019 | Okushima et al. | |
| 2020/0179267 | A1 * | 6/2020 | Shah | A61K 47/12 |
| 2022/0401373 | A1 | 12/2022 | Honjo et al. | |

FOREIGN PATENT DOCUMENTS

| | | | | |
|---|---|---|---|---|
| EP | 1787640 | A1 * | 5/2007 | A61P 9/06 |
| WO | 2005/105045 | | 11/2005 | |
| WO | 2017/060861 | | 4/2017 | |
| WO | 2017/217494 | | 12/2017 | |
| WO | 2020/255837 | | 12/2020 | |

OTHER PUBLICATIONS

International Search Report issued Feb. 1, 2022 in International (PCT) Application No. PCT/JP2021/044592.

* cited by examiner

*Primary Examiner* — Sean M Basquill
(74) *Attorney, Agent, or Firm* — Wenderoth, Lind & Ponack, L.L.P.

(57) ABSTRACT

In masking particles comprising a drug-containing particle containing a drug of a salt with an acid and containing a carbonate, the drug-containing particle being coated with a coating layer containing a water-insoluble polymer, drug release in the oral cavity and pharynx is sufficiently suppressed, the drug is rapidly released after swallowing, and the release suppression time of the drug is easily controlled. The drug-containing particle may comprise a core particle and an interlayer on the core particle, and the core particle may contain the drug of a salt with an acid, and the interlayer contains the carbonate, or the core particle may contain the carbonate, and the interlayer may contain the drug of a salt with an acid.

14 Claims, 5 Drawing Sheets

TIMED-ELUTION MASKING PARTICLES AND ORAL PHARMACEUTICAL COMPOSITION CONTAINING THE SAME

TECHNICAL FIELD

The present invention relates to masking particles that suppress drug release in the oral cavity or pharynx, but do not suppress drug release in the stomach or intestines, and can control drug release and to an oral pharmaceutical composition comprising the masking particles. More specifically, the present invention relates to masking particles that reduce a drug taste, especially the taste of a drug having an unpleasant taste sensed at the time of taking, and to an oral pharmaceutical composition comprising the masking particles.

BACKGROUND ART

Tablets and capsules are generally used as oral pharmaceutical preparations but are difficult for elderly persons and children having low swallowing function to swallow. To address this disadvantage, orally disintegrating tablets that rapidly disintegrate in the oral cavity have been drawing attention because these tablets are easily swallowed and can be taken without water. However, the orally disintegrating tablets disintegrate in the oral cavity, and thus orally disintegrating tablets containing a drug having an unpleasant taste such as bitterness could strongly give the unpleasant taste, unfortunately. Granules, fine granules, powders, and similar dosage forms are smaller in size than tablets and capsules and thus are easily swallowed. However, these preparations have a large surface area per weight, and thus a preparation containing a drug having an unpleasant taste could strongly give the unpleasant taste, unfortunately.

Orally disintegrating tablets, granules, fine granules, powders, and similar dosage forms rapidly release a drug on contact with water in the oral cavity. Hence, some drugs are absorbed through the oral cavity or pharynx, and the blood concentration suddenly increases to cause unexpected side effects, or pharmaceutical effects vary, unfortunately.

To mask the unpleasant taste of a pharmaceutical ingredient sensed at the time of taking or to suppress the absorption of a pharmaceutical ingredient from the oral cavity or pharynx, granules, fine granules, powders, tablets, and similar dosage forms have been coated with a coating agent containing a water-insoluble polymer. When an oral pharmaceutical preparation is coated, any taste of the pharmaceutical ingredient is not sensed in the mouth, and any pharmaceutical ingredient is not absorbed from the oral cavity or pharynx. However, the coating delays the drug release, and accordingly, the drug may be insufficiently absorbed and may fail to achieve an intended pharmaceutical effect.

A drug is thought to be absorbed mainly from the small intestine. Therefore, the drug is required to be released before it reaches the small intestine or while it is retained in the small intestine.

The degree of unpleasant taste and the absorption pattern vary with the type of drug, and the residence time in the oral cavity varies with the dosage form of a preparation. Hence, the release suppression time is preferably controllable to an intended time.

Patent Literature 1 discloses, as an oral pharmaceutical composition that suppresses drug release in the oral cavity, a granular pharmaceutical composition comprising a core particle containing a drug having an unpleasant taste, at the center, a layer containing two types of water-soluble ingredients, an insolubilizing accelerator and a substance to be insolubilized, as an interlayer, and a water infiltration control layer as the outermost layer. The interlayer contains a salting out-type insolubilizing accelerator and a substance to be insolubilized by salting out or contains an acid-type insolubilizing accelerator and a substance to be insolubilized by the acid. According to Patent Literature 1, water does not infiltrate for a predetermined period of time into the granular composition, which is ascribable to the water infiltration control layer, and the insolubilizing accelerator helps insolubilization of the substance to be insolubilized to suppress drug dissolution, but after that, water infiltrates to release the insolubilizing accelerator, and accordingly the substance to be insolubilized recovers its intrinsic water-solubility. As a result, the drug is released.

However, the granular pharmaceutical composition taught by Patent Literature 1 is difficult to control the release suppression time of a drug to an intended time, and especially, the drug dissolution is delayed.

CITATION LIST

Patent Literature

Patent Literature 1: JP 4277904 B

SUMMARY OF INVENTION

Technical Problem

The present invention has objectives to provide masking particles that sufficiently suppress drug release in the oral cavity and pharynx, rapidly release a drug after swallowing, and easily control the release suppression time of a drug and to provide an oral pharmaceutical composition comprising the masking particles.

Solution to Problem

The inventors of the present invention have repeated intensive studies in order to solve the above problems and have found that masking particles in which particles containing a drug of a salt with an acid and containing a carbonate are coated with a coating layer containing a water-insoluble polymer suppress the drug dissolution in the mouth or at the pharynx ascribable to the presence of the coating layer, but subsequently, rapidly release the drug of a salt with an acid because water gradually infiltrates through the coating layer into the masking particles to cause reaction between the drug of a salt with an acid and the carbonate, and the resulting foaming destroys the masking particles.

The present invention has been completed on the basis of the above findings and provides the following [1] to [14].

[1] Masking particles comprising a drug-containing particle containing a drug of a salt with an acid and containing a carbonate, the drug-containing particle being coated with a coating layer containing a water-insoluble polymer.

[2] The masking particles according to [1], wherein the carbonate is at least one water-soluble carbonate.

[3] The masking particles according to [1] or [2], wherein the carbonate is contained in an amount of 0.1 to 50% by weight relative to a total amount of the drug-containing particles.

[4] The masking particles according to any one of [1] to [3], wherein the carbonate is contained in an amount of 0.001 to 10 parts by weight relative to 1 part by weight of the drug of a salt with an acid.

[5] The masking particles according to any one of [1] to [4], wherein a content of the coating layer is 0.01 to 1 part by weight relative to 1 part by weight of the drug-containing particles.

[6] The masking particles according to any one of [1] to [5], wherein the drug-containing particle is a uniform particle containing the drug of a salt with an acid and containing the carbonate.

[7] The masking particles according to any one of [1] to [5], wherein the drug-containing particle comprises a portion containing the drug of a salt with an acid and a separate portion containing the carbonate.

[8] The masking particles according to [7], wherein the drug-containing particle comprises a core particle and an interlayer on the core particle, and the core particle contains the drug of a salt with an acid, and the interlayer contains the carbonate, or the core particle contains the carbonate, and the interlayer contains the drug of a salt with an acid.

[9] The masking particles according to [8], further comprising a separating layer between the core particle and the interlayer of the drug-containing particle.

[10] The masking particles according to [8] or [9], wherein the core particle contains a disintegrant.

[11] The masking particles according to any one of [8] to [10], wherein the interlayer or the interlayer and the separating layer contain a binder and/or a fluidizer or lubricant.

[12] A tablet, a capsule, granules, fine granules, or a powder comprising the masking particles according to any one of [1] to [11].

[13] An orally disintegrating tablet comprising the masking particles according to any one of [1] to [11].

[14] A method of producing masking particles, the method comprising a step of coating a drug-containing particle containing a drug of a salt with an acid and containing a carbonate with a coating layer containing a water-insoluble polymer.

[15] A method of controlling dissolution or release of a drug from particles containing the drug, the method comprising coating a drug-containing particle containing a drug of a salt with an acid and containing a carbonate with a coating layer containing a water-insoluble polymer.

Advantageous Effects of Invention

In masking particles of the present invention, each particle containing a drug of a salt with an acid is coated with a coating layer containing a water-insoluble polymer, and thus the drug taste is not sensed or is suppressed in the mouth. Hence, the masking particles can be suitably used to produce a pharmaceutical composition containing a drug that is in the form of a salt with an acid and has an unpleasant taste such as bitterness.

The masking particles of the present invention can be suitably used as granules, fine granules, or powders, which are typical dosage forms likely to give the drug taste in the mouth, and the resulting preparation does not give or is unlikely to give the taste of a drug of a salt with an acid in the mouth.

The masking particles of the present invention can also be used to produce tablets. When the masking particles of the present invention are used to produce orally disintegrating tablets, the drug taste is not sensed or is unlikely to be sensed in the mouth because the particles containing a drug of a salt with an acid are coated. Coating tablets to suppress the drug taste generally fails to yield orally disintegrating tablets, but using the masking particles of the present invention enables the production of orally disintegrating tablets that suppress the taste of a drug of a salt with an acid.

In the masking particles of the present invention, each particle containing a drug of a salt with an acid is coated with a coating layer containing a water-insoluble polymer, and thus the release of the drug by contact with water in the oral cavity is suppressed. Accordingly, the absorption of the drug from the oral cavity or pharynx is suppressed. This prevents unexpected side effects caused by the absorption of the drug from the oral cavity or pharynx and prevents variation in efficacy among individuals.

The masking particles of the present invention suppress the absorption of a drug of a salt with an acid from the oral cavity or pharynx and thus can be suitably used for the production of preparations soluble in the stomach or intestines.

After swallowing of the masking particles of the present invention, water in the digestive tract gradually infiltrates into the coating layer, and the water entering into the particles rapidly causes a reaction between a drug of a salt with an acid and a carbonate. The resulting foaming destroys the masking particles to release the drug. This mechanism enables sufficient absorption of the drug from the small intestine. This mechanism also enables sufficient exertion of pharmaceutical effects of a drug targeting the intestines, such as a digestant, a drug for controlling intestinal function, an intestinal analgesic and antispasmodic, and a deforming agent.

The masking particles of the present invention can release a drug at an intended time by adjusting the type of water-insoluble polymer, the thickness of the coating layer, the types and the amounts of the drug of a salt with an acid and the carbonate, the types and the amounts of other ingredients, the layer structure of the drug-containing particles, and other conditions. Hence, the drug release suppression time can be appropriately controlled according to the type of a drug of a salt with an acid or a dosage form.

In the presence of water, a drug of a salt with an acid rapidly reacts with a carbonate to cause foaming, and thus the masking particles of the present invention can accurately control the drug release suppression time. This enables the production of a preparation having an intended drug release pattern depending on a drug or a dosage form.

A pharmaceutical composition containing the masking particles of the present invention has excellent storage stability, and the performance is unlikely to deteriorate even when the pharmaceutical composition is stored in a high humidity condition. In other words, the pharmaceutical composition maintains a performance over a long time such that the composition is not destroyed in the oral cavity or at the pharynx and then is rapidly destroyed to release the drug.

BRIEF DESCRIPTION OF DRAWINGS

FIG. 10(A) shows the results of Examples 19 to 21 in which sodium hydrogen carbonate was used as the carbonate; and FIG. 10(B) shows the results in Examples 22 to 24 in which sodium carbonate was used as the carbonate.

FIG. 12(A) shows the results of Example 20 in which sodium hydrogen carbonate was used as the carbonate; and FIG. 12(B) shows the results of Example 23 in which sodium carbonate was used as the carbonate.

DESCRIPTION OF EMBODIMENTS

Figure 1:
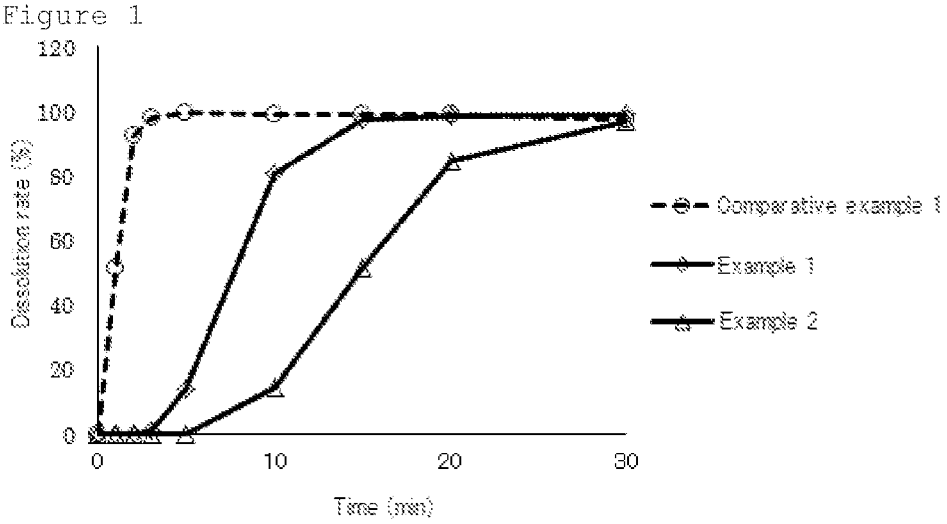
FIG. 1 is a graph showing the dissolution test results of sitagliptin phosphate from masking particles of Examples 1 and 2 and drug-containing particles of Comparative Example 1.

The present invention will now be described in detail.

Masking particles of the present invention are particles in which particles containing a drug of a salt with an acid and containing a carbonate are each coated with a coating layer containing a water-insoluble polymer. The masking particles of the present invention can be used singly or be mixed with excipients to yield tablets, granules, fine granules, powders, or the like. The masking particles may also be made into capsules (hard capsules, soft capsules) with a capsule base material.

In the present invention, a granular portion containing a drug of a salt with an acid and containing a carbonate is called a "drug-containing particle", and a particle prepared by coating the "drug-containing particle" with a coating layer containing a water-insoluble polymer is called a "masking particle". As described later, the granular portion containing a drug of a salt with an acid and containing a carbonate (the portion except the coating layer) may be a particle having a uniform formula or may comprise a central core and a layer surrounding the central core. In each case, the portion except the coating layer is called a "drug-containing particle".

Drug of Salt with Acid

The drug of a salt with an acid is not specifically limited. The drug may be any drug that reacts with a carbonate to generate carbonic acid, and typically, a drug having a smaller pKa than that of carbonic acid may be used. The acid may be either an organic acid or an inorganic acid. The drug of a salt with an acid is also called a drug as an acid addition salt.

Examples of the salt include inorganic acid salts such as a hydrochloride, a sulfate, a phosphate, a nitrate, and a hydrobromide; and organic acid salts such as an acetate, a maleate, a fumarate, a tartrate, a succinate, a malate, an oxalate, a citrate, a stearate, a gluconate, a malonate, a mesylate, an esylate, a besylate, a tosylate, a benzoate, a methyl sulfate, a lauryl sulfate, and a pamoate.

The drug of a salt with an acid may be either an anhydride or a hydrate.

Examples of the drug of a salt with an acid include the following salts.

Examples of the hydrochloride include dl-methylephedrine hydrochloride, l-isoproterenol hydrochloride, L-cysteine ethyl ester hydrochloride, L-cysteine methyl ester hydrochloride, aclarubicin hydrochloride, acotiamide hydrochloride hydrate, azasetron hydrochloride, acebutolol hydrochloride, azelastine hydrochloride, atomoxetine hydrochloride, anagrelide hydrochloride hydrate, apraclonidine hydrochloride, aprindine hydrochloride, opium alkaloid hydrochloride, apomorphine hydrochloride hydrate, amantadine hydrochloride, amiodarone hydrochloride, amitriptyline hydrochloride, aminolevulinic acid hydrochloride, amrubicin hydrochloride, amoslarol hydrochloride, amorolfine hydrochloride, alprenolol hydrochloride, alectinib hydrochloride, arotinolol hydrochloride, ambroxol hydrochloride, isoxsuprine hydrochloride, isoproterenol hydrochloride, idarubicin hydrochloride, itopride hydrochloride, ivabradine hydrochloride, imidapril hydrochloride, irinotecan hydrochloride hydrate, indisetron hydrochloride, indeloxazine hydrochloride, esmolol hydrochloride, etafenone hydrochloride, ethambutol hydrochloride, ethylmorphine hydrochloride hydrate, etilefrine hydrochloride, etelcalcetide hydrochloride, epinastine hydrochloride, epirubicin hydrochloride, ephedrine hydrochloride, eprazinone hydrochloride, eperisone hydrochloride, erlotinib hydrochloride, oxycodone hydrochloride hydrate, oxytetracycline hydrochloride, oxybutynin hydrochloride, oxybuprocaine hydrochloride, oxymetazoline hydrochloride, oxprenolol hydrochloride, ozagrel hydrochloride hydrate, olprinone hydrochloride hydrate, olodaterol hydrochloride, olopatadine hydrochloride, ondansetron hydrochloride hydrate, capmatinib hydrochloride hydrate, carteolol hydrochloride, carpipramine hydrochloride hydrate, quizartinib hydrochloride, quinapril hydrochloride, quinine hydrochloride hydrate, guanfacine hydrochloride, gusperimus hydrochloride, granisetron hydrochloride, clindamycin hydrochloride, clenbuterol hydrochloride, clocapramine hydrochloride hydrate, clonidine hydrochloride, clofedanol hydrochloride, cloperastine hydrochloride, clomipramine hydrochloride, chlorpromazine hydrochloride, chlorhexidine hydrochloride, ketamine hydrochloride, gemcitabine hydrochloride, cocaine hydrochloride, colforsin daropate hydrochloride, sapropterin hydrochloride, sarpogrelate hydrochloride, cyclopentolate hydrochloride, dicyclomine hydrochloride, cinacalcet hydrochloride, dipivefrin hydrochloride, difenidol hydrochloride, diphenylpyraline hydrochloride, diphenhydramine hydrochloride, dibucaine hydrochloride, ciprofloxacin hydrochloride, cyproheptadine hydrochloride hydrate, dilazep hydrochloride hydrate, diltiazem hydrochloride, spectinomycin hydrochloride hydrate, sultopride hydrochloride, cetirizine hydrochloride, cetraxate hydrochloride, cevimeline hydrochloride hydrate, cefetamet pivoxil hydrochloride, cefepime hydrochloride hydrate, cefozopran hydrochloride, cefotiam hydrochloride, cefcapene pivoxil hydrochloride hydrate, cefmenoxime hydrochloride, sevelamer hydrochloride, celiprolol hydrochloride, sertraline hydrochloride, selegiline hydrochloride, sotalol hydrochloride, daunorubicin hydrochloride, daclatasvir hydrochloride, tapentadol hydrochloride, tamsulosin hydrochloride, talampicillin hydrochloride, talipexole hydrochloride, tiapride hydrochloride, thiamine chloride hydrochloride, ticlopidine hydrochloride, tizanidine hydrochloride, tipiracil hydrochloride, tirabrutinib hydrochloride, tilisolol hydrochloride, tulobuterol hydrochloride, dexmedetomidine hydrochloride, tetracaine hydrochloride, tetracycline hydrochloride, tetrahydrozoline hydrochloride, tepotinib hydrochloride hydrate, demethylchlorotetracycline hydrochloride, temocapril hydrochloride, duloxetine hydrochloride, delapril hydrochloride, terbinafine hydrochloride, doxapram hydrochloride hydrate, doxycycline hydrochloride hydrate, doxorubicin hydrochloride, donepezil hydrochloride, dopamine hydrochloride, dobutamine hydrochloride, trazodone hydrochloride, tramazoline hydrochloride, tramadol hydrochloride, trientine hydrochloride, triprolidine hydrochloride hydrate, trihexyphenidyl hydrochloride, trimetazidine hydrochloride, trimethoquinol hydrochloride hydrate, dorzolamide hydrochloride, tolperisone hydrochloride, tropisetron hydrochloride, naphazoline hydrochloride, naratriptan hydrochloride, nalfurafine hydrochloride, nalmefene hydrochloride hydrate, naloxone hydrochloride, nicardipine hydrochloride, nifekalant hydrochloride, nilotinib hydrochloride hydrate, neticonazole hydrochloride, nogitecan hydrochloride, nortriptyline hydrochloride, bacampicillin hydrochloride, pazopanib hydrochloride, papaverine hydrochloride, valacyclovir hydrochloride, valganciclovir hydrochloride, vardenafil hydrochloride hydrate, barnidipine hydrochloride, paroxetine hydrochloride hydrate, palonosetron hydrochloride, vancomycin hydrochloride, pioglitazone hydrochloride, hydralazine hydrochloride, hydroxyzine hydrochloride, hydromorphone hydrochloride, pipamperone hydrochloride, bifemelane hydrochloride, pivmecillinam hydrochloride, pipethanate hydrochloride, biperiden hydrochloride, piperidolate hydrochloride, pirarubicin hydrochloride, pyridoxine hydrochloride, pilsicainide hydrochloride hydrate, pirmenol hydrochloride hydrate, pirenzepine hydrochloride hydrate, pilocarpine hydrochloride, piroheptine hydrochloride, pseudoephedrine hydrochloride, fasudil hydrochloride, fasudil hydrochloride hydrate, fadrozole hydrochloride hydrate, fingolimod hydrochloride, fexofenadine hydrochloride, phenylephrine hydrochloride, forodesine hydrochloride, butenafine hydrochloride, bunazosin hydrochloride, bupivacaine hydrochloride hydrate, bufetolol hydrochloride, buprenorphine hydrochloride, buformin hydrochloride, prasugrel hydrochloride, prazosin hydrochloride, flavoxate hydrochloride, pramipexole hydrochloride hydrate, pralmorelin hydrochloride, fursultiamin hydrochloride, flunarizine hydrochloride, bleomycin hydrochloride, procainamide hydrochloride, procaine hydrochloride, procaterol hydrochloride hydrate, procarbazine hydrochloride, proguanil hydrochloride, propafenone hydrochloride, propitocaine hydrochloride, propiverine hydrochloride, propranolol hydrochloride, bromhexine hydrochloride, promethazine hydrochloride, beclabuvir hydrochloride, betaxolol hydrochloride, pethidine hydrochloride, benazepril hydrochloride, benidipine hydrochloride, bevantolol hydrochloride, bepridil hydrochloride hydrate, verapamil hydrochloride, perphenazine hydrochloride, perospirone hydrochloride hydrate, benserazide hydrochloride, pentazocine hydrochloride, bendamustine hydrochloride, venlafaxine hydrochloride, ponatinib hydrochloride, fominoben hydrochloride, homochlorcyclizine hydrochloride, mazaticol hydrochloride hydrate, manidipine hydrochloride, mabuterol hydrochloride, maprotiline hydrochloride, mianserin hydrochloride, migalastat hydrochloride, mitoxantrone hydrochloride, midodrine hydrochloride, milnacipran hydrochloride, mexiletine hydrochloride, meclofenoxate hydrochloride, methadone hydrochloride, methixene hydrochloride, methylephedrine hydrochloride, methylphenidate hydrochloride, methoxamine hydrochloride, methoxyphenamine hydrochloride, metformin hydrochloride, mepivacaine hydrochloride, mefloquine hydrochloride, memantine hydrochloride, moxisylyte hydrochloride, moxifloxacin hydrochloride, mozavaptan hydrochloride, mosapramine hydrochloride, morphine hydrochloride hydrate, lascufloxacin hydrochloride, ranitidine hydrochloride, labetalol hydrochloride, ramosetron hydrochloride, raloxifene hydrochloride, landiolol hydrochloride, lysozyme hydrochloride, ritodrine hydrochloride, ripasudil hydrochloride hydrate, rilpivirine hydrochloride, rilmazafone hydrochloride hydrate, lincomycin hydrochloride hydrate, lurasidone hydrochloride, lenampicillin hydrochloride, levocabastine hydrochloride, levocetirizine hydrochloride, levobunolol hydrochloride, levobupivacaine hydrochloride, levomepromazine hydrochloride, remifentanil hydrochloride, roxatidine acetate hydrochloride, ropinirole hydrochloride, ropivacaine hydrochloride hydrate, loperamide hydrochloride, lomefloxacin hydrochloride, and lomerizine hydrochloride.

Examples of the sulfate include atropine sulfate hydrate, abacavir sulfate, amikacin sulfate, arbekacin sulfate, isepamicin sulfate, isoproterenol sulfate, enviomycin sulfate, orciprenaline sulfate, kanamycin sulfate, quinidine sulfate hydrate, clopidogrel sulfate, gentamicin sulfate, salbutamol sulfate, dibekacin sulfate, streptomycin sulfate, cefoselis sulfate, ceftolozane sulfate, cefpirome sulfate, terbutaline sulfate, paromomycin sulfate, hydroxychloroquine sulfate, vincristine sulfate, vinblastine sulfate, fradiomycin sulfate, bleomycin sulfate, protamine sulfate, peplomycin sulfate, berberine sulfate hydrate, bekanamycin sulfate, polymyxin B sulfate, micronomicin sulfate, morphine sulfate hydrate, and ribostamycin sulfate.

Examples of the phosphate include oseltamivir phosphate, codeine phosphate hydrate, disopyramide phosphate, sitagliptin phosphate hydrate, dihydrocodeine phosphate, dimemorfan phosphate, primaquine phosphate, benproperine phosphate, and ruxolitinib phosphate.

Examples of the nitrate include isoconazole nitrate, econazole nitrate, oxiconazole nitrate, sulconazole nitrate, tetrahydrozoline nitrate, naphazoline nitrate, and miconazole nitrate.

Examples of the hydrobromide include teneligliptin hydrobromide hydrate.

Examples of the acetate include icatibant acetate, indacaterol acetate, caspofungin acetate, ganirelix acetate, guanabenz acetate, glatiramer acetate, goserelin acetate, gonadorelin acetate, cetrorelix acetate, degarelix acetate, desmopressin acetate hydrate, tetracosactide acetate, teriparatide acetate, bazedoxifene acetate, hydroxocobalamin acetate, vilanterol trifenatate, buserelin acetate, flecainide acetate, lanreotide acetate, and leuprorelin acetate.

Examples of the maleate include dl-chlorpheniramine maleate, d-chlorpheniramine maleate, asenapine maleate, afatinib maleate, irsogladine maleate, indacaterol maleate, enalapril maleate, ergometrine maleate, carpipramine maleate, chlorpheniramine maleate, setiptiline maleate, timolol maleate, trifluoperazine maleate, trimebutine maleate, filgotinib maleate, fluphenazine maleate, fluvoxamine maleate, proglumetacin maleate, perphenazine maleate, methylergometrine maleate, and levomepromazine maleate.

Examples of the fumarate include alafenamide fumarate, aliskiren fumarate, emedastine fumarate, gilteritinib fumarate, quetiapine fumarate, clemastine fumarate, ketotifen fumarate, tenofovir alafenamide fumarate, tenofovir disoproxil fumarate, nizofenone fumarate, bisoprolol fumarate, fesoterodine fumarate, brovincamine fumarate, bedaquiline fumarate, vonoprazan fumarate, formoterol fumarate hydrate, and rupatadine fumarate.

Examples of the tartrate include alimemazine tartrate, ifenprodil tartrate, eliglustat tartrate, ergotamine tartrate, cysteamine tartrate, zolpidem tartrate, tolterodine tartrate, varenicline tartrate, vinorelbine tartrate, brimonidine tartrate, protirelin tartrate hydrate, metoprolol tartrate, and levallorphan tartrate.

Examples of the succinate include cibenzoline succinate, sumatriptan succinate, solifenacin succinate, and trelagliptin succinate.

Examples of the malate include cabozantinib malate and sunitinib malate.

Examples of the oxalate include escitalopram oxalate.

Examples of the citrate include clomiphene citrate, diethylcarbamazine citrate, sildenafil citrate, tamoxifen citrate, tandospirone citrate, tofacitinib citrate, toremifene citrate, fentanyl citrate, pentoxyverine citrate, and mosapride citrate hydrate.

Examples of the stearate include erythromycin stearate.

Examples of the gluconate include chlorhexidine gluconate.

Examples of the malonate include bopindolol malonate.

Examples of the mesylate include adrenochrome monoaminoguanidine mesylate hydrate, imatinib mesylate, eribulin mesylate, osimertinib mesylate, gabexate mesylate, camostat mesylate, garenoxacin mesylate hydrate, saquinavir mesylate, dihydroergotamine mesylate, dihydroergotoxine mesylate, dabrafenib mesylate, delavirdine mesylate, deferoxamine mesylate, doxazosin mesylate, nafamostat mesylate, nelfinavir mesylate, pazufloxacin mesylate, phentolamine mesylate, pridinol mesylate, bromocriptine mesylate, betahistine mesylate, pergolide mesylate, rasagiline mesylate, lisdexamfetamine mesylate, lenvatinib mesylate, and lomitapide mesylate.

Examples of the esylate include nintedanib ethanesulfonate.

Examples of the besylate include amlodipine besylate, bepotastine besilate, mirogabalin besylate, and remimazolam besylate.

Examples of the tosylate include edoxaban tosylate hydrate, suplatast tosylate, sultamicillin tosylate hydrate, tosufloxacin tosylate hydrate, naldemedine tosylate, niraparib tosylate hydrate, and lapatinib tosylate hydrate.

Examples of the benzoate include rizatriptan benzoate.

Examples of the methyl sulfate include amezinium methyl sulfate and neostigmine methyl sulfate.

Examples of the lauryl sulfate include diphenhydramine lauryl sulfate.

Examples of the pamoate include pasireotide pamoate.

The drug of a salt with an acid may be used singly or in combination of two or more of them.

A drug that is not a salt with an acid may also be used as long as the effect of the invention is not impaired.

The content of the drug of a salt with an acid varies with the drug, but is preferably 1% by weight or more, more preferably 10% by weight or more, even more preferably 20% by weight or more, and still more preferably 25% by weight or more relative to the total amount of the drug-containing particles. The content is preferably 85% by weight or less, more preferably 75% by weight or less, even more preferably 65% by weight or less, and still more preferably 60% by weight or less. Within the above range, reaction with a carbonate in the stomach or intestines can rapidly destroy masking particles, and the drug can be released.

Carbonate

The carbonate may be any pharmaceutically acceptable carbonate, and examples of the water-soluble carbonate include sodium carbonate, potassium carbonate, sodium hydrogen carbonate, potassium hydrogen carbonate, and ammonium carbonate. Examples of the water-insoluble or poorly water-soluble carbonate include calcium carbonate and magnesium carbonate.

Of them, a water-soluble carbonate is preferred, a hydrogen carbonate is more preferred, and sodium hydrogen carbonate and potassium hydrogen carbonate are even more preferred. Using a hydrogen carbonate improves the drug release rate while an enough lag time is maintained. Using a hydrogen carbonate also improves the storage stability and is unlikely to cause performance deterioration by moisture absorption even when the masking particle or pharmaceutical composition is stored under a high humid condition, or is unlikely to cause a reduction in lag time or drug release rate over time.

The carbonates may be used singly or in combination of two or more of them.

The content of the carbonate is preferably 0.1% by weight or more, more preferably 1% by weight or more, and even more preferably 3% by weight or more relative to the total amount of the drug-containing particles. The content is preferably 50% by weight or less, more preferably 40% by weight or less, even more preferably 35% by weight or less, and still more preferably 30% by weight or less relative to the total amount of the drug-containing particles. Within the above range, reaction with a drug of a salt with an acid can rapidly destroy masking particles, and the drug can be released.

As for the content ratio of the carbonate to the drug of a salt with an acid, the content of the carbonate is preferably 0.001 part by weight or more, more preferably 0.01 part by weight or more, even more preferably 0.03 part by weight or more, and still more preferably 0.05 part by weight or more relative to 1 part by weight of the drug of a salt with an acid. The content is preferably 10 parts by weight or less, more preferably 3 parts by weight or less, and even more preferably 1.5 parts by weight or less relative to 1 part by weight of the drug of a salt with an acid. Within the above range, the salt and the carbonate can cause foaming sufficient to achieve intended drug dissolution.

Excipients

The masking particles of the present invention can contain, in the drug-containing particles, any excipients usable in tablets, granules, fine granules, powders, or the like as long as the effect of the invention is not impaired. Examples of the excipient include a diluent, a disintegrant, a binder, a lubricant or fluidizer (adhesion inhibitor), a coloring agent, a flavoring agent, a sweetening agent, and a preservative or antiseptic. The excipients may be used singly or in combination of two or more of them.

Examples of the diluent include sugars such as lactose hydrate, white soft sugar, maltose, fructose, glucose, and trehalose; sugar alcohols such as mannitol (especially, D-mannitol), maltitol, sorbitol, xylitol, erythritol, and lactitol; starches such as starch, pregelatinized starch, and partially pregelatinized starch; celluloses such as crystalline cellulose; dextrin; dextran; glycerol fatty acid esters; and inorganic powders such as magnesium aluminometasilicate and synthetic hydrotalcite.

Examples of the binder include povidone; celluloses such as methyl cellulose, ethyl cellulose, carboxymethyl cellulose, hydroxypropyl cellulose, hydroxyethyl cellulose, hydroxypropyl methyl cellulose (hypromellose), and croscarmellose sodium; starch; gelatin; polysaccharide thickeners such as agar, alginic acid, sodium alginate, tragacanth, xanthan gum, gum arabic, pullulan, and dextrin; polyvinyl alcohol-polyethylene glycol graft copolymers; carboxyvinyl polymers; polyethylene oxide; copolyvidone; polyoxyethylene hydrogenated castor oil; polymers containing a derivative in which a hydrophobic group is introduced to the N-position of N-isopropyl acrylamide and/or acrylamide; polyoxyethylene-polyoxypropylene glycol; polyvinyl alcohols (including partially saponified polyvinyl alcohols); basic (meth)acrylate copolymers; and polyethylene glycol.

Examples of the disintegrant include crospovidone; celluloses such as carboxymethyl cellulose (carmellose), carmellose sodium, carmellose calcium, low-substituted hydroxypropyl cellulose, croscarmellose sodium, and crystalline cellulose; starches such as starch, pregelatinized starch, partially pregelatinized starch, sodium carboxymethyl starch, sodium carboxy starch, and hydroxypropyl starch; dextrin; calcium silicate; calcium citrate; and light anhydrous silicic acid.

Examples of the lubricant or fluidizer (adhesion inhibitor) include stearic acid, stearates (such as magnesium stearate, calcium stearate, aluminum stearate, and zinc stearate), sodium stearyl fumarate, glyceryl monostearate, glyceryl palmitostearate, sodium lauryl sulfate, polyethylene glycol, talc, glycerol fatty acid esters, sucrose fatty acid esters, sodium potassium tartrate, carnauba wax, L-leucine, polyethylene glycol, hardened oil, silicic acid compounds (such as light anhydrous silicic acid, magnesium aluminometasilicate, hydrated silicon dioxide, and synthetic aluminum silicate), and titanium oxide.

Examples of the coloring agent include yellow ferric oxide, red ferric oxide, titanium oxide, black iron oxide, edible tar dyes, natural pigments (such as β-carotene and riboflavin).

Examples of the sweetening agent include sucralose, mannitol, sucrose, aspartame, *stevia*, and acesulfame potassium.

Examples of the preservative or antiseptic include ethyl p-hydroxybenzoate, propyl p-hydroxybenzoate, butyl p-hydroxybenzoate, benzoic acid, and sodium benzoate.

Coating Layer

The coating layer contains a water-insoluble polymer usable as the coating agent in pharmaceutical preparations. In the present invention, the "water-insoluble polymer" includes polymers poorly soluble in water, in addition to polymers completely insoluble in water.

Examples of the water-insoluble polymer include cellulose coating agents (such as methyl cellulose, ethyl cellulose, hydroxyethyl cellulose, carboxymethyl ethyl cellulose, sodium carboxymethyl cellulose, hypromellose phthalate, hypromellose acetate succinate, cellulose acetate, and cellulose acetate phthalate), vinyl polymers (such as polyvinyl acetal diethylamino acetate and polyvinyl acetate phthalate), methacrylate polymers or methacrylic acid polymers, and polysiloxane coating agents (such as dimethylpolysiloxane and dimethylpolysiloxane-silicon dioxide mixtures).

Of them, a methacrylate polymer or methacrylic acid polymer and a cellulose coating agent (especially, ethyl cellulose) are preferred, and a methacrylate polymer or methacrylic acid polymer is more preferred.

The methacrylate polymer or methacrylic acid polymer is available as various commercial products, and examples include EUDRAGIT E series, EUDRAGIT L series, EUDRAGIT S series, EUDRAGIT R series, EUDRAGIT NE series, and EUDRAGIT FS series (registered trademark) manufactured by Roehm GmbH. Specific examples include aminoalkyl methacrylate copolymer E (such as EUDRAGITs E100 and EPO), methacrylic copolymer LD (such as EUDRAGITs L30D-55 and L100-55), methacrylic acid copolymer L (such as EUDRAGIT L100), methacrylic acid copolymer S (such as EUDRAGIT S100), aminoalkyl methacrylate copolymer (such as EUDRAGITs RL100, RLPO, RS100, RSPO, RL30D, and RS30D), and ethyl acrylate-methyl methacrylate copolymer (such as EUDRAGIT NE30D).

The water-insoluble polymer is classified, for example, into pH-independent polymers, enteric polymers, and gastro-soluble polymers. In the present invention, any water-insoluble polymer can be preferably used and can be selected so as to achieve an intended release suppression time for a drug. As described in a section in examples, in the masking particles of the present invention, water gradually infiltrates through the coating layer to cause the reaction between a drug of a salt with an acid and a carbonate, and the resulting foaming destroys the masking particles. For example, even when an enteric polymer is used, this mechanism also enables the dosage form design to release a drug before the masking particles reach the intestines.

The coating layer can contain excipients such as a plasticizer, a binder, a fluidizer or lubricant (adhesion inhibitor), a coloring agent, and a sweetening agent as long as the effect of the invention is not impaired. The excipients may be used singly or in combination of two or more of them.

Examples of the plasticizer include glycerol fatty acid esters such as polyethylene glycol, propylene glycol, glycerol, and triacetin (glycerol triacetate), liquid paraffin, sorbitan monolaurate, monostearin, triethyl citrate, tributyl citrate, diethyl phthalate, dibutyl phthalate, diethyl sebacate, dibutyl sebacate, poloxamer, and polyoxyethylene hydrogenated castor oil.

Examples of the binder, the fluidizer or lubricant (adhesion inhibitor), the coloring agent, and the sweetening agent include those exemplified as the excipients for the drug-containing particles.

The content of the coating layer is preferably 0.01 part by weight or more, more preferably 0.02 part by weight or more, and even more preferably 0.03 part by weight or more relative to 1 part by weight of the drug-containing particles. The content is preferably 1 part by weight or less, more preferably 0.7 part by weight or less, even more preferably 0.6 part by weight or less, and still more preferably 0.4 part by weight or less. Within the above range, water infiltrates at an appropriate speed, the drug release in the oral cavity or at the pharynx is sufficiently suppressed, and subsequently, the drug can be rapidly released.

Particle Structure

In the masking particles of the present invention, each drug-containing particle containing a drug of a salt with an acid and containing a carbonate is at least coated with a coating layer containing a water-insoluble polymer, and the masking particle can have various structures.

First Embodiment

The masking particles can be, for example, particles in which each uniform or single-structure drug-containing particle containing a drug of a salt with an acid and containing a carbonate is coated with a coating layer. In the embodiment, the drug of a salt with an acid and the carbonate are contained in the same portion, and thus water infiltrating through the coating layer can very rapidly cause foaming to release the drug. The drug-containing particles can further contain any excipients usable in tablets, granules, fine granules, powders, or the like.

Second Embodiment

The masking particles can be particles in which each drug-containing particle comprising a portion containing a drug of a salt with an acid and a separate portion containing a carbonate is coated with a coating layer.

A drug of a salt with an acid and a carbonate contained in the same portion cause foaming when dissolved. Hence, water cannot be used in the production process, and the production method may be limited. To address this disadvantage, for example, a drug-containing particle consisting of a core particle and an interlayer can be coated with a coating layer to give a masking particle, and the core particle and the interlayer can separately contain any of the drug of a salt with an acid and the carbonate. In this case, the drug of a salt with an acid and the carbonate are separately present in different portions, and thus one or both of the core particle and the interlayer can be formed by using water. In particular, an aqueous solution of the interlayer material can be used for coating (interlayer formation).

The drug of a salt with an acid and the carbonate may be contained in any of the core particle and the interlayer. Preferably, the core particle contains the drug of a salt with an acid, and the interlayer contains the carbonate, because, for example, this structure allows the use of a coating layer unstable to acid.

In each case, the core particle can consist of a central core containing a diluent or the like and a layer surrounding the central core. This structure helps the production of spherical drug-containing particles. Accordingly, the coating layer is easily formed, and drug-containing particles having a narrow particle size distribution can be produced.

Between the core particle and the interlayer, one or more other interlayers (the layer separates a drug-containing portion and a carbonate-containing portion and thus is called a "separating layer" hereinafter) are preferably provided. This structure prevents the drug of a salt with an acid from reacting with the carbonate before administration of the masking particles or a pharmaceutical composition containing the masking particles and can improve the stability of the drug of a salt with an acid or a drug product.

Between the interlayer and the coating layer, one or more other interlayer (hereinafter called a "cover layer") may be provided.

The drug-containing particles in the second embodiment may consist of a core particle containing neither the drug of a salt with an acid nor the carbonate, an interlayer containing the drug of a salt with an acid, and an additional interlayer containing the carbonate. The interlayer containing the drug of a salt with an acid and the interlayer containing the carbonate may be either inside or outside. Between the interlayer containing the drug of a salt with an acid and the interlayer containing the carbonate, one or more separating layers are preferably provided. On the outside of the interlayer containing the drug of a salt with an acid and the interlayer containing the carbonate, one or more cover layers may be provided. Between the core particle and the interlayer containing the drug of a salt with an acid or the interlayer containing the carbonate, one or more other interlayers (hereinafter called "underlayers") may be provided.

In the second embodiment, the core particle, the interlayer, the separating layer, the cover layer, and the underlayer may further contain any excipient usable in granules, fine granules, powders, or the like.

Specifically, when the core particle contains a disintegrant, the water absorbability of the disintegrant facilitates water infiltration, and thus the drug of a salt with an acid readily reacts with the carbonate. The disintegrant is preferably crospovidone or a cellulose such as carboxymethyl cellulose (carmellose), carmellose sodium, carmellose calcium, low-substituted hydroxypropyl cellulose, and crystalline cellulose, and is more preferably low-substituted hydroxypropyl cellulose. The content of the disintegrant is preferably about 0.5 to 50% by weight relative to the total amount of the drug-containing particles.

The interlayer, the separating layer, the cover layer, and the underlayer preferably contain a binder to facilitate the layer formation. The binder is preferably hydroxypropyl cellulose, hydroxypropyl methyl cellulose (hypromellose), or polyethylene glycol. The total content of the binder in the drug-containing particles is preferably about 0.1 to 20% by weight relative to the total amount of the drug-containing particles.

The interlayer, the separating layer, the cover layer, and the underlayer preferably contain a fluidizer or lubricant (adhesion inhibitor) to suppress the electrification of particles for a smooth production process. In the drug-containing particles, the total content of the fluidizer or lubricant is preferably about 0.01 to 50% by weight relative to the total amount of the drug-containing particles.

The masking particles of the present invention can be particles having various structures in addition to these embodiments.

Production Method

The masking particles of the present invention can be produced by a method comprising a step of coating drug-containing particles containing a drug of a salt with an acid and containing a carbonate with a coating layer containing a water-insoluble polymer.

The drug-containing particles, the core particles, and the central cores containing a diluent can be produced in a common procedure by wet or dry granulation and as needed by drying and rounding. Examples of the wet granulation include fluidized-bed granulation, agitation granulation, tumbling granulation, extrusion granulation, crushing granulation, kneading granulation, continuous direct granulation, and complex fluidized-bed granulation. Examples of the dry granulation include dry complex granulation, roller compaction dry granulation, briquette granulation, and melt granulation.

The interlayer and the coating layer can be produced in a common procedure by using a machine such as a fluidized-bed coating machine, a Wurster fluidized-bed coating machine, a centrifugal fluidized-bed coating machine, and a tumbling fluidized-bed coating machine.

Properties

The drug-containing particle has various shapes depending on granulation methods and can be spherical, cylindrical, prolate spherical (prolate elliptic), or the like.

The particle size of the masking particles after coating with the coating layer is not limited to particular values, and the $D_{50}$ can be about 50 to 1,000 μm, specifically about 100 to 800 μm. In the present invention, the $D_{50}$ is a particle size measured and calculated in accordance with the particle size determination by laser diffractometry in the particle size determination described in the Japanese Pharmacopoeia, Seventeenth Edition.

Tablets

The masking particles of the present invention can be used to produce tablets. Accordingly, the present invention also provides a tablet produced by using the masking particles of the present invention. The tablet can be produced, for example, by directly tableting the masking particles of the present invention or by tableting a mixture with one or more excipients.

The masking particles of the present invention mask a drug taste sensed in the mouth and thus can be suitably used to produce orally disintegrating tablets. Various methods of producing the orally disintegrating tablet are known, and a person skilled in the art can produce orally disintegrating tablets by appropriately selecting the types and the amounts of excipients to be mixed with the masking particles of the present invention.

When the masking particles of the present invention are mixed with excipients to produce an orally disintegrating tablet, the content of the masking particles of the present invention can be 1% by weight or more, 5% by weight or more, or 10% by weight or more relative to the total amount of the orally disintegrating tablet. The content can be 90% by weight or less, 70% by weight or less, or 60% by weight or less.

Drug Dissolution Rate

The masking particles of the present invention have various dissolution rates depending on the type of a drug of a salt with an acid, but the dissolution rate determined by using a pH 6.8 dissolution test solution in accordance with the paddle method in the dissolution test described in the Japanese Pharmacopoeia, Seventeenth Edition, is preferably substantially 0 (substantially no drug is dissolved) for at least 0.5 minute, specifically for at least 1 minute, specifically for at least 1.5 minutes, or specifically for at least 3 minutes after the start of the test.

The masking particles of the present invention can have release lag time of a drug of a salt with an acid of 0.5 minute or more, 1 minute or more, or 2 minutes or more. The drug release lag time can be 15 minutes or less, 12 minutes or less, 10 minutes or less, or 8 minutes or less. The drug release lag time is a value determined by the method described in a section in examples.

The masking particles of the present invention preferably have a drug release rate of 1%/min or more, specifically 2%/min or more, specifically 5%/min or more. The drug release rate can be 80%/min or less, 70%/min or less, 60%/min or less, 50%/min or less, 30%/min or less, or 20%/min or less. The drug release rate is a value determined by the method described in a section in EXAMPLES.

Drug Dissolution Control Method

The present invention encompasses a method of delaying dissolution or release of a drug of a salt with an acid from drug-containing particles (for a predetermined period of time) or a method of suppressing dissolution or release (for a predetermined period of time) of a drug of a salt with an acid, by coating drug-containing particles containing the drug of a salt with an acid and containing a carbonate with a coating layer containing a water-insoluble polymer. By the method, the drug dissolution suppression time can be controlled by selecting the types, amounts, and ratios of the drug of a salt with an acid, the carbonate, and other ingredients contained in the drug-containing particles; the amount of the coating layer; the types, amounts, and ratios of ingredients contained in the coating layer; and other conditions. The types, amounts, and ratios of the drug of a salt with an acid, the carbonate, and other ingredients contained in the drug-containing particles; the amount of the coating layer; the types, amounts, and ratios of ingredients contained in the coating layer; and other conditions are as described for the masking particles of the present invention. The present invention therefore encompasses a method of controlling drug dissolution or drug release from drug-containing particles by coating the drug-containing particles containing a drug of a salt with an acid and containing a carbonate with a coating layer containing a water-insoluble polymer.

EXAMPLES

The present invention will next be described in further detail with reference to examples, but the present invention is not limited to them.

(1) Test Method (Dissolution Test)

Dissolution test was performed in accordance with the second method of the dissolution test described in the Japanese Pharmacopoeia. The paddle rotation rate was set at 50 rpm, and 900 mL of a pH 6.8 phosphate buffer solution (the second solution of the disintegration test in the Japanese Pharmacopoeia) was used as the test solution. Drug-containing particles, masking particles, or tablets containing 124.1 mg of sitagliptin phosphate were placed in a vessel. At testing times of 1, 2, 3, 5, 6, 7, 8, 10, 12, 15, 20, 30 minutes, 10 mL of the solution was sampled from each vessel, and the dissolution rate was determined by ultraviolet-visible spectrophotometry. The measurement was repeated three times, and the average was calculated as an average dissolution rate.

(Particle Size Distribution Measurement)

In the present invention, the particle size is determined by using a laser diffraction particle size analyzer (manufactured by Malvern) based on volume.

(2) Evaluation of Drug Dissolution

Examples 1 and 2 (Masking Particles)

Drug-containing particles comprising a core particle containing sitagliptin phosphate, a separating layer containing a binder and a lubricant, and an interlayer containing sodium hydrogen carbonate and masking particles in which the drug-containing particles were coated were produced by the following procedures.

Preparation of Core Particles

In an agitation mixing granulator, 249.1 g of sitagliptin phosphate, 15.1 g of low-substituted hydroxypropyl cellulose (manufactured by Shin-Etsu Chemical; LHPC31, hereinafter the same applies), and 35.9 g of hydroxypropyl cellulose (manufactured by Nippon Soda; HPCL fine powder, hereinafter the same applies) were placed and mixed. While the whole was stirred, a mixed liquid of 21 g of ethanol (manufactured by Japan Alcohol, hereinafter the same applies) and 21 g of purified water was then sprayed, and the whole was granulated. The product was then sieved, and particles passed through a 60-mesh (250 μm) sieve but not passed through a 140-mesh (106 μm) sieve were collected as core particles.

Preparation of Coating Liquid (1)

To a solution of 15.8 g of hydroxypropyl cellulose (manufactured by Nippon Soda; HPCSL, hereinafter the same applies) in 221.6 g of ethanol and 95 g of purified water, 41.2 g of talc (manufactured by NIPPON TALC; MICRO ACE P3, hereinafter the same applies) was added, and the whole was stirred to give a coating liquid (1).

Preparation of Separating Layer-Coated Particles

In a tumbling fluidized-bed coating machine, 179.4 g of the core particles were placed, and the coating liquid (1) was sprayed to give separating layer-coated particles.

Preparation of Coating Liquid (2)

To a solution of 35.4 g of hydroxypropyl cellulose (manufactured by Nippon Soda; HPCL, hereinafter the same applies) in 707.7 g of absolute ethanol, 70.8 g of talc and 130.9 g of pulverized sodium hydrogen carbonate (manufactured by AGC, hereinafter the same applies) were added, and the whole was stirred to give a coating liquid (2).

Preparation of Drug-Containing Particles

In a tumbling fluidized-bed coating machine, 207.8 g of the separating layer-coated particles were placed, and the coating liquid (2) was sprayed to give drug-containing particles.

Preparation of Coating Liquid (3)

In a mixed liquid of 1,184 g of ethanol and 132 g of purified water, 132 g of aminoalkyl methacrylate copolymer E (manufactured by Evonik Nutrition & Care GmbH; EUDRAGIT E, hereinafter the same applies) was dissolved, and 132 g of talc was added. The whole was stirred to give a coating liquid (3).

Preparation of Masking Particles

In a tumbling fluidized-bed coating machine, 328.9 g of the drug-containing particles were placed, and the coating liquid (3) was sprayed to give masking layer-coated particles.

Particles having the masking layer (a coating layer containing a water-insoluble polymer is called a "masking layer"; the same applies hereinafter) at a mass ratio of 4% relative to the mass of the drug-containing particles were regarded as Example 1, and particles having the masking layer at a mass ratio of 8% were regarded as Example 2.

In each of Examples 1 and 2, the content of sodium hydrogen carbonate was 1 part by weight relative to 1 part by weight of sitagliptin phosphate and was 29.4% by weight relative to the total amount of the drug-containing particles.

Comparative Example 1

A similar procedure to that for Examples 1 and 2 was performed to give drug-containing particles as Comparative Example 1.

The formulae of the particles of Examples 1 and 2 and Comparative Example 1 are shown in Table 1.

TABLE 1

(Unit: mg)

| | Ingredient | Comparative Example 1 | Example 1 | Example 2 |
|---|---|---|---|---|
| Core particle | Sitagliptin phosphate | 124.1 | 124.1 | 124.1 |
| | Low-substituted hydroxypropyl cellulose | 7.5 | 7.5 | 7.5 |
| | Hydroxypropyl cellulose | 17.9 | 17.9 | 17.9 |
| Separating layer | Talc | 34.3 | 34.3 | 34.3 |
| | Hydroxypropyl cellulose | 13.2 | 13.2 | 13.2 |
| Interlayer | Sodium hydrogen carbonate | 124.1 | 124.1 | 124.1 |
| | Talc | 67.1 | 67.1 | 67.1 |
| | Hydroxypropyl cellulose | 33.5 | 33.5 | 33.5 |
| Masking layer | Aminoalkyl methacrylate copolymer E | 0 | 8.4 | 16.9 |
| | Talc | 0 | 8.4 | 16.9 |
| Total | | 421.7 | 438.5 | 455.5 |

(Evaluation Results)

The particles of Examples 1 and 2 and Comparative Example 1 were subjected to the dissolution test. Changes in dissolution rate of sitagliptin phosphate are shown in FIG. 1.

In Comparative Example 1, the drug release was rapid by foaming, but no drug release lag time was observed because the particles lacked the coating layer containing a water-insoluble polymer. In contrast, in Examples 1 and 2, the coating layer containing a water-insoluble polymer prevented water infiltration for a certain period of time, and then water infiltrated. The resulting foaming caused membrane disruption from the inside to rapidly release the drug. As a result, both lag times of 2.9 to 5.3 minutes and rapid drug release rates of 7.5 to 13.4%/min were satisfied.

The drug release lag time is a time until 1% of a drug is released in the dissolution test at pH 6.8 and was calculated from two measurement time points between which 1% was interposed.

The drug release rate was calculated from two measurement time points between which a dissolution rate of 30% was interposed, in the dissolution test at pH 6.8.

Example 3 (Masking Particles)

Preparation of Core Particles

A similar procedure to that for Example 1 was performed to give core particles.

Preparation of Separating Layer-Coated Particles

A similar procedure to that for Example 1 was performed to give separating layer-coated particles.

Preparation of Coating Liquid (4)

To a solution of 20.1 g of hydroxypropyl cellulose in 402.7 g of absolute ethanol, 40.3 g of talc and 74.5 g of pulverized sodium hydrogen carbonate were added, and the whole was stirred to give a coating liquid (4).

Preparation of Drug-Containing Particles

In a tumbling fluidized-bed coating machine, 157.6 g of the separating layer-coated particles were placed, and the coating liquid (4) was sprayed to give drug-containing particles.

Preparation of Masking Particles

In a tumbling fluidized-bed coating machine, 248.6 g of the drug-containing particles were placed, and the coating liquid (3) was sprayed to give masking layer-coated particles.

The particles had the masking layer at a mass ratio of 10% relative to the mass of the drug-containing particles.

The content of sodium hydrogen carbonate was 0.75 part by weight relative to 1 part by weight of sitagliptin phosphate and was 25.5% by weight relative to the total amount of the drug-containing particles.

Comparative Example 2

A similar procedure to that for Example 3 was performed to give drug-containing particles as Comparative Example 2.

The formulae of the particles of Example 3 and Comparative Example 2 are shown in Table 2.

TABLE 2

(Unit: mg)

| | Ingredient | Comparative Example 2 | Example 3 |
|---|---|---|---|
| Core particle | Sitagliptin phosphate | 124.1 | 124.1 |
| | Low-substituted hydroxypropyl cellulose | 7.5 | 7.5 |
| | Hydroxypropyl cellulose | 17.9 | 17.9 |
| Separating layer | Talc | 34.3 | 34.3 |
| | Hydroxypropyl cellulose | 13.2 | 13.2 |
| Interlayer | Sodium hydrogen carbonate | 93.1 | 93.1 |
| | Talc | 50.3 | 50.3 |
| | Hydroxypropyl cellulose | 25.2 | 25.2 |
| Masking layer | Aminoalkyl methacrylate copolymer E | 0 | 18.3 |
| | Talc | 0 | 18.3 |
| Total | | 365.6 | 402.1 |

(Evaluation Results)

Figure 2:
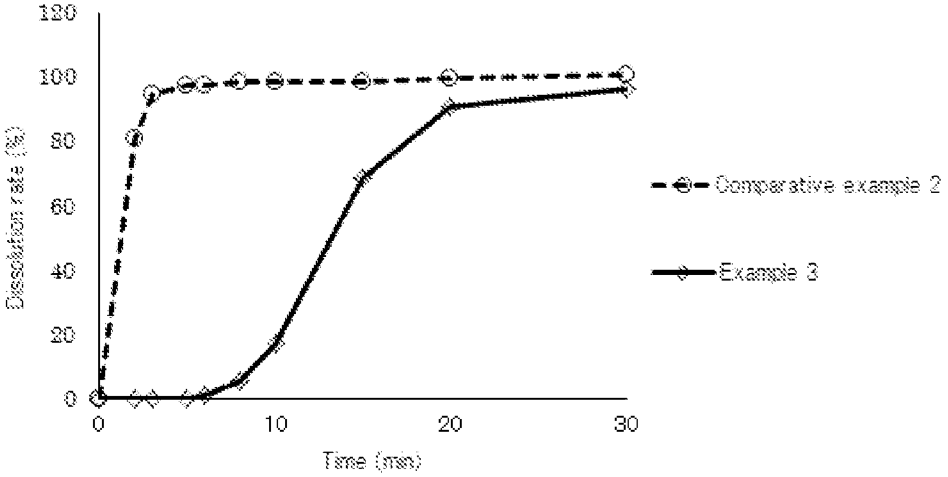
FIG. 2 is a graph showing the dissolution test results of sitagliptin phosphate from masking particles of Example 3 and drug-containing particles of Comparative Example 2. The used masking particles contained a carbonate at a smaller content than the masking particles in FIG. 1.

The particles of Example 3 and Comparative Example 2 were subjected to the dissolution test. Changes in dissolution rate of sitagliptin phosphate are shown in FIG. 2.

In Comparative Example 2, the drug release was rapid by foaming, but no drug release lag time was observed because the particles lacked the coating layer containing a water-insoluble polymer. In contrast, in Example 3, the coating layer containing a water-insoluble polymer prevented water infiltration for a certain period of time, and then water infiltrated. The resulting foaming caused membrane disruption from the inside to rapidly release the drug. As a result, both a lag time of 6.0 minutes and a rapid drug release rate of 10.3%/min were satisfied.

Examples 4 to 6 (Masking Particles)

Preparation of Core Particles

A similar procedure to that for Example 1 was performed to give core particle.

Preparation of Separating Layer-Coated Particles

A similar procedure to that for Example 1 was performed to give separating layer-coated particles.

Preparation of Coating Liquid (5)

To a solution of 14.4 g of hydroxypropyl cellulose in 288.6 g of absolute ethanol, 28.8 g of talc and 53.4 g of pulverized sodium hydrogen carbonate were added, and the whole was stirred to give a coating liquid (5).

Preparation of Drug-Containing Particles

In a tumbling fluidized-bed coating machine, 169.4 g of the separating layer-coated particles were placed, and the coating liquid (5) was sprayed to give drug-containing particles.

Preparation of Masking Particles

In a tumbling fluidized-bed coating machine, 222.3 g of the drug-containing particles were placed, and the coating liquid (3) was sprayed to give masking layer-coated particles.

Particles having the masking layer at a mass ratio of 8% relative to the mass of the drug-containing particles were regarded as Example 4; particles having the masking layer at a mass ratio of 14% were regarded as Example 5; and particles having the masking layer at a mass ratio of 18% were regarded as Example 6.

In each of Examples 4 to 6, the content of sodium hydrogen carbonate was 0.5 part by weight relative to 1 part by weight of sitagliptin phosphate and was 20.1% by weight relative to the total amount of the drug-containing particles.

Comparative Example 3

A similar procedure to that for Examples 4 to 6 was performed to give drug-containing particles as Comparative Example 3.

The formulae of the particles of Examples 4 to 6 and Comparative Example 3 are shown in Table 3.

TABLE 3

(Unit: mg)

| | Ingredient | Comparative Example 3 | Example 4 | Example 5 | Example 6 |
|---|---|---|---|---|---|
| Core particle | Sitagliptin phosphate | 124.1 | 124.1 | 124.1 | 124.1 |
| | Low-substituted hydroxypropyl cellulose | 7.5 | 7.5 | 7.5 | 7.5 |
| | Hydroxypropyl cellulose | 17.9 | 17.9 | 17.9 | 17.9 |
| Separating layer | Talc | 34.3 | 34.3 | 34.3 | 34.3 |
| | Hydroxypropyl cellulose | 13.2 | 13.2 | 13.2 | 13.2 |
| Interlayer | Sodium hydrogen carbonate | 62.1 | 62.1 | 62.1 | 62.1 |
| | Talc | 33.5 | 33.5 | 33.5 | 33.5 |
| | Hydroxypropyl cellulose | 16.8 | 16.8 | 16.8 | 16.8 |
| Masking layer | Aminoalkyl methacrylate copolymer E | 0 | 12.4 | 21.7 | 27.8 |
| | Talc | 0 | 12.4 | 21.7 | 27.8 |
| Total | | 309.4 | 334.2 | 352.8 | 365.0 |

(Evaluation Results)

Figure 3:
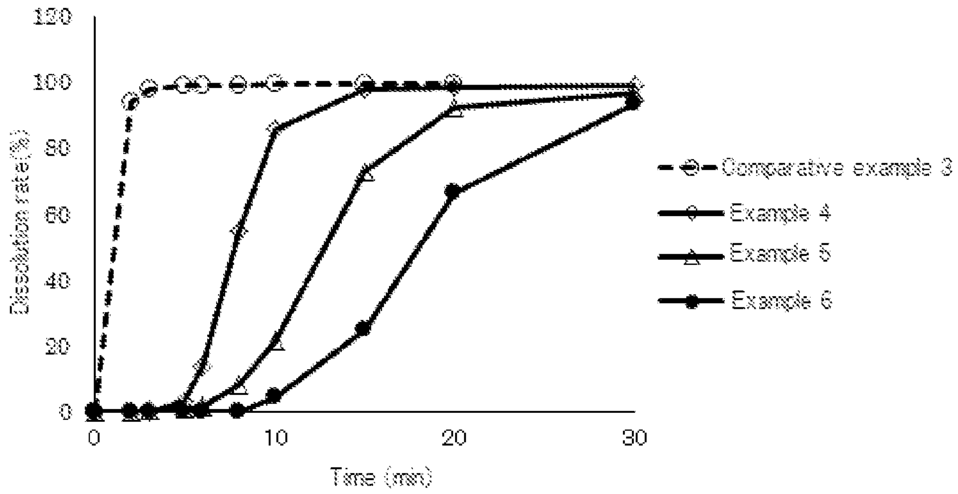
FIG. 3 is a graph showing the dissolution test results of sitagliptin phosphate from masking particles of Examples 4 to 6 and drug-containing particles of Comparative Example 3. The used masking particles contained a carbonate at a smaller content than the masking particles in FIG. 2.

The particles of Examples 4 to 6 and Comparative Example 3 were subjected to the dissolution test. Changes in dissolution rate of sitagliptin phosphate are shown in FIG. 3.

In Comparative Example 3, the drug release was rapid by foaming, but no drug release lag time was observed because the particles lacked the coating layer containing a water-insoluble polymer. In contrast, in Examples 4 to 6, the coating layer containing a water-insoluble polymer prevented water infiltration for a certain period of time, and then water infiltrated. The resulting foaming caused membrane disruption from the inside to rapidly release the drug. As a result, both lag times of 3.6 to 8.4 minutes and rapid drug release rates of 8.3 to 20.5%/min were satisfied.

Examples 7 and 8 (Masking Particles)

Preparation of Core Particles

A similar procedure to that for Example 1 was performed to give core particles.

Preparation of Separating Layer-Coated Particles

A similar procedure to that for Example 1 was performed to give separating layer-coated particles.

Preparation of Coating Liquid (6)

To a solution of 8.4 g of hydroxypropyl cellulose in 167.7 g of absolute ethanol, 16.8 g of talc and 31 g of pulverized sodium hydrogen carbonate were added, and the whole was stirred to give a coating liquid (6).

Preparation of Drug-Containing Particles

In a tumbling fluidized-bed coating machine, 197 g of the separating layer-coated particles were placed, and the coating liquid (6) was sprayed to give drug-containing particles.

Preparation of Masking Particles

In a tumbling fluidized-bed coating machine, 215.2 g of the drug-containing particles were placed, and the coating liquid (3) was sprayed to give masking layer-coated particles.

Particles having the masking layer at a mass ratio of 20% relative to the mass of the drug-containing particles were regarded as Example 7; and particles having the masking layer at a mass ratio of 24% were regarded as Example 8.

In each of Examples 7 and 8, the content of sodium hydrogen carbonate was 0.25 part by weight relative to 1 part by weight of sitagliptin phosphate and was 12.2% by weight relative to the total amount of the drug-containing particles.

Comparative Example 4

A similar procedure to that for Examples 7 and 8 was performed to give drug-containing particles as Comparative Example 4.

The formulae of the particles of Examples 7 and 8 and Comparative Example 4 are shown in Table 4.

TABLE 4

| (Unit: mg) | | | | |
|---|---|---|---|---|
| | Ingredient | Comparative Example 4 | Example 7 | Example 8 |
| Core particle | Sitagliptin phosphate | 124.1 | 124.1 | 124.1 |
| | Low-substituted hydroxypropyl cellulose | 7.5 | 7.5 | 7.5 |
| | Hydroxypropyl cellulose | 17.9 | 17.9 | 17.9 |
| Separating layer | Talc | 34.3 | 34.3 | 34.3 |
| | Hydroxypropyl cellulose | 13.2 | 13.2 | 13.2 |
| Interlayer | Sodium hydrogen carbonate | 31.0 | 31.0 | 31.0 |
| | Talc | 16.8 | 16.8 | 16.8 |
| | Hydroxypropyl cellulose | 8.4 | 8.4 | 8.4 |
| Masking layer | Aminoalkyl methacrylate copolymer E | 0 | 25.3 | 30.4 |
| | Talc | 0 | 25.3 | 30.4 |
| Total | | 253.2 | 303.8 | 314.0 |

(Evaluation Results)

Figure 4:
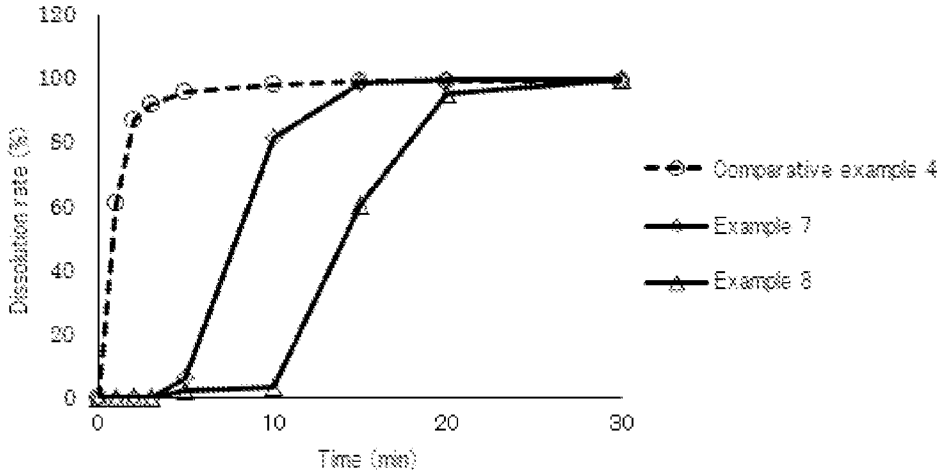
FIG. 4 is a graph showing the dissolution test results of sitagliptin phosphate from masking particles of Examples 7 and 8 and drug-containing particles of Comparative Example 4. The used masking particles contained a carbonate at a smaller content than the masking particles in FIG. 3.

The particles of Examples 7 and 8 and Comparative Example 4 were subjected to the dissolution test. Changes in dissolution rate of sitagliptin phosphate are shown in FIG. 4.

In Comparative Example 4, the drug release was rapid by foaming, but no drug release lag time was observed because the particles lacked the coating layer containing a water-insoluble polymer. In contrast, in Examples 7 and 8, the coating layer containing a water-insoluble polymer prevented water infiltration for a certain period of time, and then water infiltrated. The resulting foaming caused membrane disruption from the inside to rapidly release the drug. As a result, both lag times of 3.3 to 4.0 minutes and rapid drug release rates of 11.4 to 15.1%/min were satisfied.

Example 9 (Masking Particles)

Preparation of Core Particles

A similar procedure to that for Example 1 was performed to give core particles.

Preparation of Separating Layer-Coated Particles

A similar procedure to that for Example 1 was performed to give separating layer-coated particles.

Preparation of Coating Liquid (7)

To a solution of 2.0 g of hydroxypropyl cellulose in 41 g of absolute ethanol, 4.1 g of talc and 7.6 g of pulverized sodium hydrogen carbonate were added, and the whole was stirred to give a coating liquid (7).

Preparation of Drug-Containing Particles

In a tumbling fluidized-bed coating machine, 192.5 g of the separating layer-coated particles were placed, and the coating liquid (7) was sprayed to give drug-containing particles.

Preparation of Masking Particles

In a tumbling fluidized-bed coating machine, 175.2 g of the drug-containing particles were placed, and the coating liquid (3) was sprayed to give masking layer-coated particles.

The particles had the masking layer at a mass ratio of 36% relative to the mass of the drug-containing particles.

The content of sodium hydrogen carbonate was 0.06 part by weight relative to 1 part by weight of sitagliptin phosphate and was 3.7% by weight relative to the total amount of the drug-containing particles.

Comparative Example 5

A similar procedure to that for Example 9 was performed to prepare drug-containing particles as Comparative Example 5.

The formulae of the particles of Example 9 and Comparative Example 5 are shown in Table 5.

TABLE 5

| (Unit: mg) | | | |
|---|---|---|---|
| | Ingredient | Comparative Example 5 | Example 9 |
| Core particle | Sitagliptin phosphate | 124.1 | 124.1 |
| | Low-substituted hydroxypropyl cellulose | 7.5 | 7.5 |
| | Hydroxypropyl cellulose | 17.9 | 17.9 |
| Separating layer | Talc | 34.3 | 34.3 |
| | Hydroxypropyl cellulose | 13.2 | 13.2 |
| Interlayer | Sodium hydrogen carbonate | 7.8 | 7.8 |
| | Talc | 4.2 | 4.2 |
| | Hydroxypropyl cellulose | 2.1 | 2.1 |
| Masking layer | Aminoalkyl methacrylate copolymer E | 0 | 38.0 |
| | Talc | 0 | 38.0 |
| Total | | 211.1 | 287.0 |

(Evaluation Results)

Figure 5:
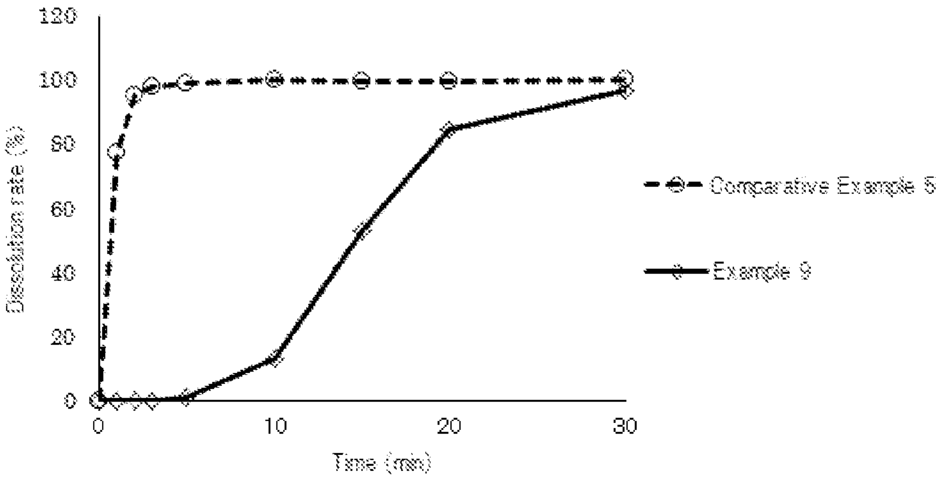
FIG. 5 is a graph showing the dissolution test results of sitagliptin phosphate from masking particles of Example 9 and drug-containing particles of Comparative Example 5. The used masking particles contained a carbonate at a smaller content than the masking particles in FIG. 4.

The particles of Example 9 and Comparative Example 5 were subjected to the dissolution test. Changes in dissolution rate of sitagliptin phosphate are shown in FIG. 5.

In Comparative Example 5, the drug release was rapid by foaming, but no drug release lag time was observed because the particles lacked the coating layer containing a water-insoluble polymer. In contrast, in Example 9, the coating layer containing a water-insoluble polymer prevented water infiltration for a certain period of time, and then water infiltrated. The resulting foaming caused membrane disruption from the inside to rapidly release the drug. As a result, both a lag time of 5.0 minutes and a rapid drug release rate of 7.9%/min were satisfied.

Example 10 (Orally Disintegrating Tablets)

Preparation of Rapidly Disintegrating Granules

In a fluidized-bed granulator (Powrex; MP-01, hereinafter the same applies), 660 g of D-mannitol, 20 g of ethyl cellulose, 10 g of light anhydrous silicic acid, 200 g of corn starch, 90 g of crospovidone, and 900 g of purified water were granulated to give rapidly disintegrating granules.

Preparation of Tablets

To a mixture of 365.03 mg of the masking particles of Example 6, 365.03 mg of the rapidly disintegrating particles, 7.73 mg of light anhydrous silicic acid, and 30 mg of aspartame, 5.82 mg of magnesium stearate was added and mixed. The mixture was placed in a single punch tableting machine (Ichihashi Seiki; HANDTAB-200, hereinafter the same applies) and was tableted by using a 12-mm punch, giving tablets having a tablet thickness of 6.07 mm.

Figure 6:
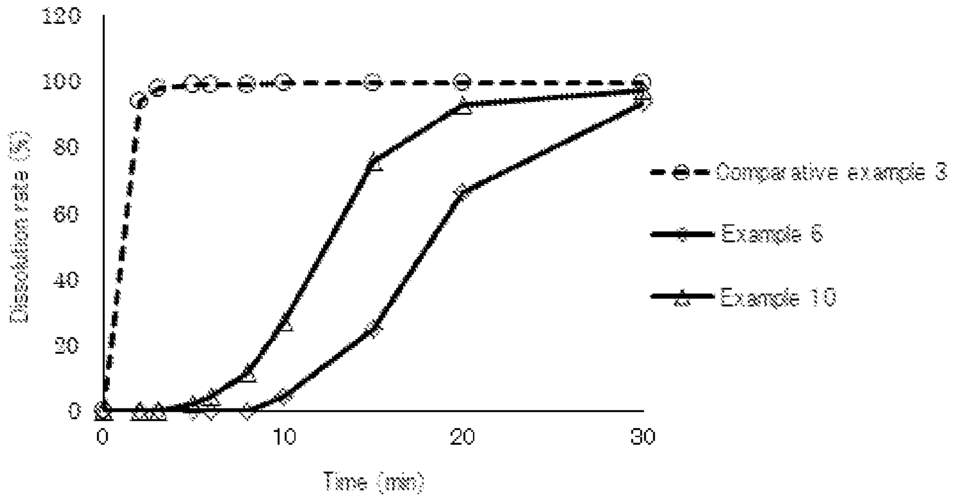
FIG. 6 is a graph showing the dissolution test results of sitagliptin phosphate from orally disintegrating tablets of Example 10, masking particles of Example 6, and drug-containing particles of Comparative Example 3.

The orally disintegrating tablets of Example 10, the masking particles of Example 6 (particles prepared by coating the drug-containing particles of Comparative Example 3 with 18% by weight of the masking layer), and the drug-containing particles of Comparative Example 3 were subjected to the dissolution test. Changes in dissolution rate of sitagliptin phosphate are shown in FIG. 6.

The lag time of the tablets of Example 10 was 3.9 minutes, which was shorter than the lag time (8.4 minutes) of the masking particles of Example 6, but was sufficient to suppress the drug dissolution in the mouth. The drug release rate of the tablets of Example 10 was 9.8%/min, which was substantially the same as the drug release rate (8.3%/min) of the masking particles of Example 6, and almost 100% of the drug was eluted 30 minutes after the start of the dissolution test.

The results reveal that the masking particles of the present invention can be used to produce tablets, and the resulting tablets suppress the drug release in the mouth and subsequently, rapidly release the drug.

The formula of the orally disintegrating tablets of Example 10 is shown in Table 6.

TABLE 6

(Unit: mg)

| | | Ingredient | Example 10 |
|---|---|---|---|
| Tablet | Masking particle | Masking particle of Example 6 | 365.0 |
| | Excipients mixture | Rapidly disintegrating granule | 365.0 |
| | | Light anhydrous silicic acid | 7.7 |
| | | Aspartame | 30.0 |
| | | Magnesium stearate | 5.8 |
| | Total | | 773.5 |

Example 11 (Masking Particles)

Preparation of Core Particles

In an agitation mixing granulator, 249.0 g of sitagliptin phosphate, 15.1 g of low-substituted hydroxypropyl cellulose, and 35.9 g of hydroxypropyl cellulose were placed and mixed. While the whole was stirred, a mixed liquid of 21 g of ethanol and 21 g of purified water was then sprayed, and the whole was granulated. The product was then sieved, and particles passed through a 30-mesh (500 μm) sieve but not passed through a 200-mesh (75 μm) sieve were considered as one batch. Two batches were produced and then mixed to give core particles.

Preparation of Coating Liquid (8)

To a solution of 98.0 g of hydroxypropyl cellulose in 1,960 g of ethanol, 254.5 g of talc was added, and the whole was stirred to give a coating liquid (8).

Preparation of Separating Layer-Coated Particles

In a tumbling fluidized-bed coating machine, 493.4 g of the core particles were placed, and the coating liquid (8) was sprayed to give separating layer-coated particles.

Preparation of Coating Liquid (9)

To a solution of 27.5 g of hydroxypropyl cellulose in 550.7 g of absolute ethanol, 55.1 g of talc and 102.2 g of pulverized sodium hydrogen carbonate were added, and the whole was stirred to give a coating liquid (9).

Preparation of Drug-Containing Particles

In a tumbling fluidized-bed coating machine, 837.5 g of the separating layer-coated particles were placed, and the coating liquid (9) was sprayed to give drug-containing particles.

Preparation of Coating Liquid (10)

In a mixed liquid of 826.8 g of ethanol and 91.9 g of purified water, 91.9 g of aminoalkyl methacrylate copolymer E was dissolved, and 91.9 g of talc was added. The whole was stirred to give a coating liquid (10).

Preparation of Masking Particles

In a fluidized-bed granulation coating machine (Freund Corporation; FL-LABO, hereinafter the same applies), 1,015 g of the drug-containing particles were placed, and the coating liquid (10) was sprayed to give masking particles.

The particles had the masking layer at a mass ratio of 17.8% relative to the mass of the drug-containing particles.

The content of sodium hydrogen carbonate was 0.24 part by weight relative to 1 part by weight of sitagliptin phosphate and was 9.7% by weight relative to the total amount of the drug-containing particles.

The formula of the masking particles of Example 11 is shown in Table 7.

TABLE 7

(Unit: mg)

| | Ingredient | Example 11 |
|---|---|---|
| Core particle | Sitagliptin phosphate | 124.1 |
| | Low-substituted hydroxypropyl cellulose | 7.5 |
| | Hydroxypropyl cellulose | 17.9 |
| Separating layer | Talc | 75.3 |
| | Hydroxypropyl cellulose | 29.0 |
| Interlayer | Sodium hydrogen carbonate | 29.7 |
| | Talc | 16.0 |
| | Hydroxypropyl cellulose | 8.0 |

TABLE 7-continued

| (Unit: mg) | | |
|---|---|---|
| | Ingredient | Example 11 |
| Masking layer | Aminoalkyl methacrylate copolymer E | 27.4 |
| | Talc | 27.4 |
| Total | | 362.3 |

Example 12 (Orally Disintegrating Tablets)

Preparation of Rapidly Disintegrating Granules

By using a fluidized bed granulator, 795 g of D-mannitol, 24 g of ethyl cellulose, 12 g of light anhydrous silicic acid, 241 g of corn starch, 108 g of crospovidone, and 1,084 g of purified water were granulated to give rapidly disintegrating granules.

Preparation of Tablets

To a mixture of 362.3 mg of the masking particles of Example 11, 365 mg of the rapidly disintegrating particles, 7.6 mg of light anhydrous silicic acid, and 30 mg of aspartame, 3.1 mg of magnesium stearate was added and mixed. The mixture was placed in a rotary tableting machine (Kikusui Seisakusho; VIRG0512SS2AZ, hereinafter the same applies) and was tableted by using a 12-mm punch, giving tablets having a tablet thickness of 6.1 mm.

The formula of the orally disintegrating tablets of Example 12 is shown in Table 8.

TABLE 8

| (Unit: mg) | | | |
|---|---|---|---|
| | | Ingredient | Example 12 |
| Tablet | Masking particle | Masking particle of Example 11 | 362.3 |
| | Excipients mixture | Rapidly disintegrating granule | 365.0 |
| | | Light anhydrous silicic acid | 7.6 |
| | | Aspartame | 30.0 |
| | | Magnesium stearate | 3.1 |
| | Total | | 768.0 |

(Evaluation Results)

Figure 7:
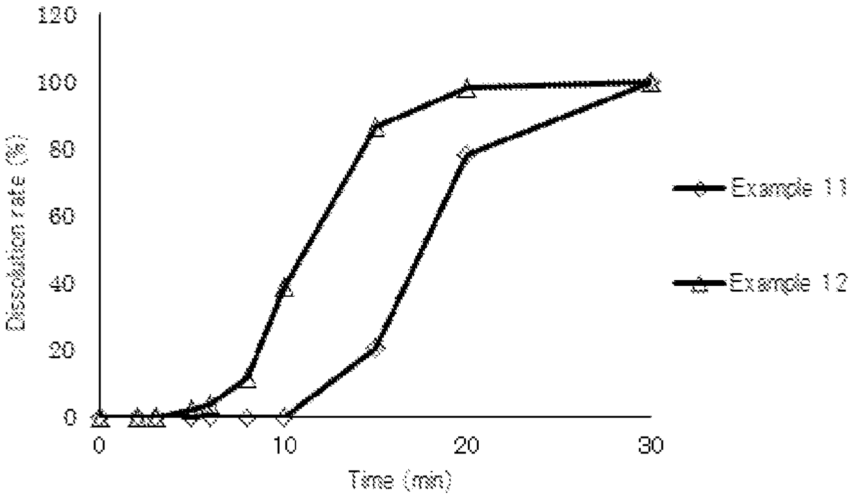
FIG. 7 is a graph showing the dissolution test results of sitagliptin phosphate from orally disintegrating tablets of Example 12 and masking particles of Example 11.

The orally disintegrating tablets of Example 12 and the masking particles of Example 11 were subjected to the dissolution test. Changes in dissolution rate of sitagliptin phosphate are shown in FIG. 7.

The lag time of the tablets of Example 12 was 3.8 minutes, which was shorter than the lag time (10.2 minutes) of the masking particles of Example 11, but was sufficient to suppress the drug dissolution in the mouth. The drug release rate of the tablets of Example 12 was 13.6%/min, which was substantially the same as the drug release rate (11.5%/min) of the masking particles of Example 11, and almost 100% of the drug was eluted 20 minutes after the start of the dissolution test.

The results reveal that the masking particles of the present invention can be used to produce tablets, and the resulting tablets suppress the drug release in the mouth and subsequently, rapidly release the drug.

Example 13 (Masking Particles)

Preparation of Core Particles

A similar procedure to that for Example 11 was performed to give core particles.

Preparation of Separating Layer-Coated Particles

A similar procedure to that for Example 11 was performed to give separating layer-coated particles.

Preparation of Coating Liquid (11)

To a solution of 55.0 g of hydroxypropyl cellulose in 1,101 g of absolute ethanol, 110.1 g of talc and 204.4 g of pulverized sodium hydrogen carbonate were added, and the whole was stirred to give a coating liquid (11).

Preparation of Drug-Containing Particles

In a tumbling fluidized-bed coating machine, 837.5 g of the separating layer-coated particles were placed, and the coating liquid (11) was sprayed to give drug-containing particles.

Preparation of Coating Liquid (12)

In a mixed liquid of 1,841 g of ethanol and 204.5 g of purified water, 204.5 g of aminoalkyl methacrylate copolymer E was dissolved, and 204.5 g of talc was added. The whole was stirred to give a coating liquid (12).

Preparation of Masking Particles

In a fluidized-bed granulation coating machine, 794.6 g of the drug-containing particle were placed, and the coating liquid (12) was sprayed to give masking particles.

The particles had the masking layer at a mass ratio of 50.7% relative to the mass of the drug-containing particles.

The content of sodium hydrogen carbonate was 0.48 part by weight relative to 1 part by weight of sitagliptin phosphate and was 16.4% by weight relative to the total amount of the drug-containing particles.

The formula of the masking particles of Example 13 is shown in Table 9.

TABLE 9

| (Unit: mg) | | |
|---|---|---|
| | Ingredient | Example 13 |
| Core particle | Sitagliptin phosphate | 124.1 |
| | Low-substituted hydroxypropyl cellulose | 7.5 |
| | Hydroxypropyl cellulose | 17.9 |
| Separating layer | Talc | 75.3 |
| | Hydroxypropyl cellulose | 29.0 |
| Interlayer | Sodium hydrogen carbonate | 59.4 |
| | Talc | 32.0 |
| | Hydroxypropyl cellulose | 16.0 |
| Masking layer | Aminoalkyl methacrylate copolymer E | 91.5 |
| | Talc | 91.5 |
| Total | | 544.2 |

Example 14 (Orally Disintegrating Tablets)

Preparation of Rapidly Disintegrating Granules

A similar procedure to that for Example 12 was performed to give rapidly disintegrating granules.

Preparation of Tablets

To a mixture of 544.2 mg of the masking particles of Example 13, 544.6 mg of the rapidly disintegrating particles, 11.6 mg of light anhydrous silicic acid, and 30 mg of aspartame, 4.6 mg of magnesium stearate was added and mixed. The mixture was placed in a rotary tableting machine and was tableted by using a 12-mm punch, giving tablets having a tablet thickness of 6.8 mm.

The formula of the orally disintegrating tablets of Example 14 is shown in Table 10.

TABLE 10

(Unit: mg)

| | | Ingredient | Example 14 |
|---|---|---|---|
| Tablet | Masking particle | Masking particle of Example 13 | 544.2 |
| | Excipients mixture | Rapidly disintegrating granule | 544.6 |
| | | Light anhydrous silicic acid | 11.6 |
| | | Aspartame | 30.0 |
| | | Magnesium stearate | 4.6 |
| | Total | | 1135.0 |

Examples 15 to 17 (Masking Particles)

Preparation of Core Particles

In an agitation mixing granulator, 250 g of bepotastine besilate, 14.7 g of low-substituted hydroxypropyl cellulose, and 29.4 g of hydroxypropyl cellulose were placed and mixed. While the whole was stirred, a mixed liquid of 11.8 g of ethanol and 11.8 g of purified water was then sprayed, and the whole was granulated. The product was then sieved, and particles passed through a 60-mesh (250 μm) sieve but not passed through a 140-mesh (106 μm) sieve were collected as core particles.

Preparation of Coating Liquid (13)

To a solution of 35.3 g of hydroxypropyl cellulose in 705 g of purified water, 91.5 g of talc was added, and the whole was stirred to give a coating liquid (13).

Preparation of Separating Layer-Coated Particles

In a tumbling fluidized-bed coating machine, 176.5 g of the core particles were placed, and the coating liquid (13) was sprayed to give separating layer-coated particles.

Preparation of Coating Liquid (14)

To a solution of 20.9 g of hydroxypropyl cellulose in 418 g of absolute ethanol, 41.80 g of talc and 77.20 g of pulverized sodium hydrogen carbonate were added, and the whole was stirred to give a coating liquid (14).

Preparation of Drug-Containing Particles

In a tumbling fluidized-bed coating machine, 202.1 g of the separating layer-coated particles were placed, and the coating liquid (14) was sprayed to give drug-containing particles.

Preparation of Masking Particles

In a tumbling fluidized-bed coating machine, 205.2 g of the drug-containing particles were placed, and the coating liquid (3) was sprayed to give masking particles.

Particles having the masking layer at a mass ratio of 10% relative to the mass of the drug-containing particles were regarded as Example 15; particles having the masking layer at a mass ratio of 14% were regarded as Example 16; and particles having the masking layer at a mass ratio of 17.5% were regarded as Example 17.

In each of Examples 15 to 17, the content of sodium hydrogen carbonate was 0.77 part by weight relative to 1 part by weight of bepotastine besilate and was 22.6% by weight relative to the total amount of the drug-containing particles.

Comparative Example 6

A similar procedure to that for Examples 15 to 17 was performed to prepare drug-containing particles as Comparative Example 6.

The formulae of the particles of Examples 15 to 17 and Comparative Example 6 are shown in Table 11.

TABLE 11

(Unit: mg)

| | Ingredient | Comparative Example 6 | Example 15 | Example 16 | Example 17 |
|---|---|---|---|---|---|
| Core particle | Bepotastine besilate | 10.0 | 10.0 | 10.0 | 10.0 |
| | Low-substituted hydroxypropyl cellulose | 0.588 | 0.588 | 0.588 | 0.588 |
| | Hydroxypropyl cellulose | 1.176 | 1.176 | 1.176 | 1.176 |
| Separating layer | Talc | 6.1 | 6.1 | 6.1 | 6.1 |
| | Hydroxypropyl cellulose | 2.35 | 2.35 | 2.35 | 2.35 |
| Interlayer | Sodium hydrogen carbonate | 7.72 | 7.72 | 7.72 | 7.72 |
| | Talc | 4.18 | 4.18 | 4.18 | 4.18 |
| | Hydroxypropyl cellulose | 2.09 | 2.09 | 2.09 | 2.09 |

TABLE 11-continued

| | | | | | |
|---|---|---|---|---|---|
| | (Unit: mg) | | | | |
| | Ingredient | Comparative Example 6 | Example 15 | Example 16 | Example 17 |
| Masking layer | Aminoalkyl methacrylate copolymer E | 0 | 1.71 | 2.39 | 3.0 |
| | Talc | 0 | 1.71 | 2.39 | 3.0 |
| Total | | 34.204 | 37.624 | 39.004 | 40.204 |

(Evaluation Results)

Figure 8:
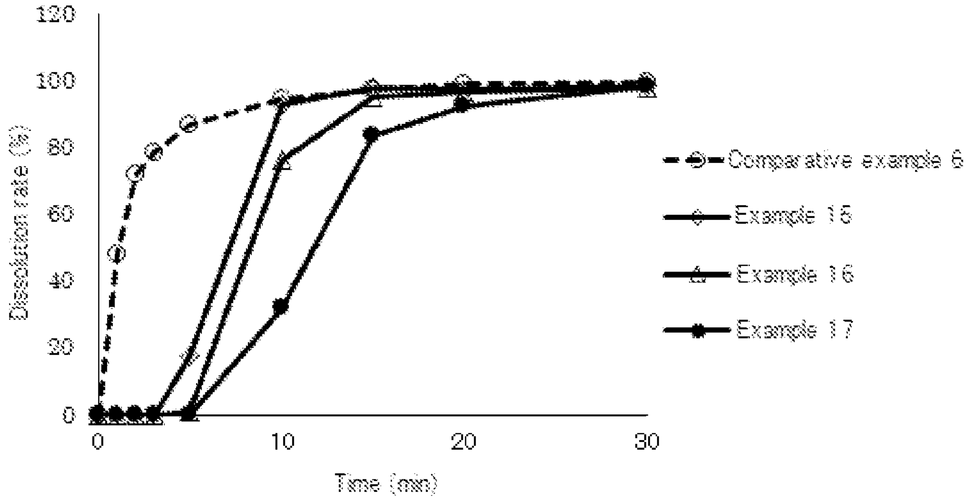
FIG. 8 is a graph showing the dissolution test results of bepotastine besilate from masking particles of Examples 15 to 17 and drug-containing particles of Comparative Example 6.

The particles of Examples 15 to 17 and Comparative Example 6 were subjected to the dissolution test. Changes in dissolution rate of bepotastine besilate are shown in FIG. 8.

In Comparative Example 6, the drug release was rapid by foaming, but no drug release lag time was observed because the particles lacked the coating layer containing a water-insoluble polymer. In contrast, in Examples 15 to 17, the coating layer containing a water-insoluble polymer prevented water infiltration for a certain period of time, and then water infiltrated. The resulting foaming caused membrane disruption from the inside to rapidly release the drug. As a result, both lag times of 3.1 to 5.2 minutes and rapid drug release rates of 6.4 to 15.1%/min were satisfied.

Example 18 (Masking Particles)

Preparation of Core Particles

In an agitation mixing granulator, 227.1 g of vonoprazan fumarate, 13.6 g of low-substituted hydroxypropyl cellulose, and 32.3 g of hydroxypropyl cellulose were placed. While the whole was stirred, a mixed liquid of 27.3 g of ethanol and 27.3 g of purified water was sprayed, and the whole was granulated. The product was then sieved, and particles passed through a 60-mesh (250 μm) sieve but not passed through a 140-mesh (106 μm) sieve were collected as core particles.

Preparation of Coating Liquid (15)

To a solution of 35.28 g of hydroxypropyl cellulose in 705.6 g of absolute ethanol, 90.72 g of talc was added, and the whole was stirred to give a coating liquid (15).

Preparation of Separating Layer-Coated Particles

In a tumbling fluidized-bed coating machine, 179.9 g of the core particles were placed, and the coating liquid (15) was sprayed to give separating layer-coated particles.

Preparation of Coating Liquid (16)

To a solution of 7.82 g of hydroxypropyl cellulose in 156 g of absolute ethanol, 15.64 g of talc and 28.06 g of pulverized sodium hydrogen carbonate were added, and the whole was stirred to give a coating liquid (16).

Preparation of Drug-Containing Particles

In a tumbling fluidized-bed coating machine, 251.25 g of the separating layer-coated particles were placed, and the coating liquid (16) was sprayed to give drug-containing particles.

Preparation of Coating Liquid (17)

In 540 g of ethanol, 60 g of aminoalkyl methacrylate copolymer E was dissolved. Separately, 7.4 g of titanium oxide (manufactured by Freund Corporation) and 0.2 g of red ferric oxide (manufactured by Kishi Kasei) were dispersed in 60 g of purified water, and the dispersion liquid was added to the ethanol solution of aminoalkyl methacrylate copolymer E. To the liquid, 60 g of talc was further added, and the whole was stirred to give a coating liquid (17).

Preparation of Masking Particles

In a tumbling fluidized-bed coating machine, 263.29 g of the drug-containing particles were placed, and the coating liquid (17) was sprayed to give masking layer-coated particles.

The particles had the masking layer at a mass ratio of 121 relative to the mass of the drug-containing particles.

The formula of the masking particles of Example 18 is shown in Table 12.

TABLE 12

| | | |
|---|---|---|
| (Unit: mg) | | |
| | Ingredient | Example 18 |
| Core particle | Vonoprazan fumarate | 26.72 |
| | Low-substituted hydroxypropyl cellulose | 1.6 |
| | Hydroxypropyl cellulose | 3.8 |
| Separating layer | Talc | 16.2 |
| | Hydroxypropyl cellulose | 6.3 |
| Interlayer | Sodium hydrogen carbonate | 6.1 |
| | Talc | 3.4 |
| | Hydroxypropyl cellulose | 1.7 |
| Masking layer | Aminoalkyl methacrylate copolymer E | 7.0 |
| | Talc | 0.86 |
| | Red ferric oxide | 0.02 |
| Total | | 73.7 |

Figure 9:
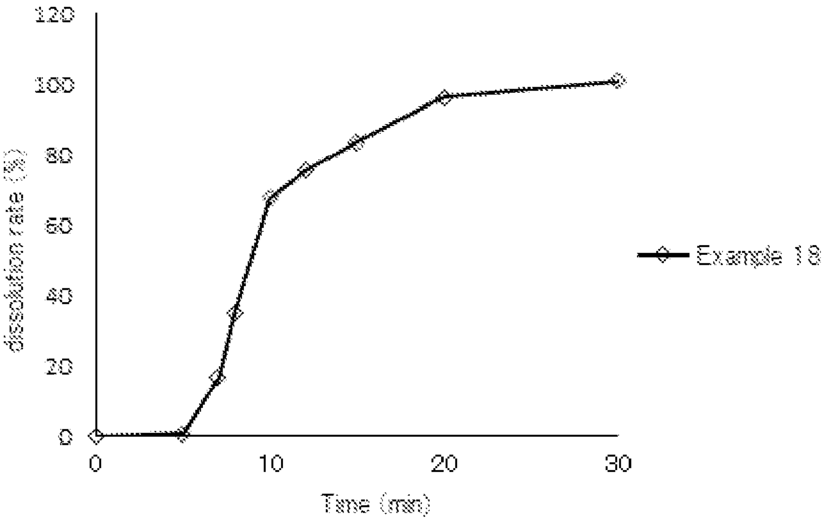
FIG. 9 is a graph showing the dissolution test results of vonoprazan fumarate from masking particles of Example 18.

The masking particles of Example 18 were subjected to the dissolution test. Changes in dissolution rate of vonoprazan fumarate are shown in FIG. 9. In Example 18, the coating layer containing a water-insoluble polymer prevented water infiltration for a certain period of time, and then water infiltrated. The resulting foaming caused membrane disruption from the inside to rapidly release the drug. As a result, both a lag time of 5.1 minutes and a rapid drug release rate of 6.2%/min were satisfied.

Example 19 (Orally Disintegrating Tablets)

Preparation of Masking Particles

In a fluidized-bed granulation coating machine, 1,015 g of the drug-containing particle of Example 11 were placed, and the coating liquid (10) was sprayed to give masking particles. The particles had the masking layer at a mass ratio of 13.9% relative to the mass of the drug-containing particles.

Preparation of Tablets

To 350.1 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 5.85 mm.

Example 20 (Orally Disintegrating Tablets)

Preparation of Masking Particles

In a fluidized-bed granulation coating machine, 1,015 g of the drug-containing particles of Example 11 were placed, and the coating liquid (10) was sprayed to give masking particles. The particles had the masking layer at a mass ratio of 17.8% relative to the mass of the drug-containing particles.

Preparation of Tablets

To 362.3 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 6.03 mm.

Example 21 (Orally Disintegrating Tablets)

Preparation of Masking Particles

In a fluidized-bed granulation coating machine, 1,015 g of the drug-containing particles of Example 11 were placed, and the coating liquid (10) was sprayed to give masking particles. The particles had the masking layer at a mass ratio of 21.8, relative to the mass of the drug-containing particles.

Preparation of Tablets

To 374.5 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 6.18 mm.

Example 22 (Orally Disintegrating Tablets)

Preparation of Coating Liquid (18)

To a solution of 27.5 g of hydroxypropyl cellulose in 550.7 g of absolute ethanol, 55.1 g of talc and 102.2 g of pulverized sodium carbonate were added, and the whole was stirred to give a coating liquid (18).

Preparation of Drug-Containing Particles

In a tumbling fluidized-bed coating machine, 837.5 g of the separating layer-coated particles of Example 11 were placed, and the coating liquid (18) was sprayed to give drug-containing particles.

Preparation of Masking Particles

In a fluidized-bed granulation coating machine, 1,015 g of the prepared drug-containing particles were placed, and the coating liquid (10) was sprayed to give masking particles. The particles had the masking layer at a mass ratio of 13.9% relative to the mass of the drug-containing particles.

Preparation of Tablets

To 350.1 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 5.85 mm.

Example 23 (Orally Disintegrating Tablets)

Preparation of Masking Particles

In a fluidized-bed granulation coating machine, 1,015 g of the drug-containing particles of Example 22 were placed, and the coating liquid (10) was sprayed to give drug-containing particles. The particles had the masking layer at a mass ratio of 17.8% relative to the mass of the drug-containing particles.

Preparation of Tablets

To 362.3 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 6.01 mm.

Example 24 (Orally Disintegrating Tablets)

Preparation of Masking Particles

In a fluidized-bed granulation coating machine, 1,015 g of the drug-containing particles of Example 22 were placed, and the coating liquid (10) was sprayed to give drug-containing particles. The particles had the masking layer at a mass ratio of 21.8% relative to the mass of the drug-containing particles.

Preparation of Tablets

To 374.5 mg of the above masking particles, 365 mg of the rapidly disintegrating particles used in Example 12, 7.6 mg of light anhydrous silicic acid, and 30 mg of aspartame were added and mixed. To the mixture, 3.1 mg of magnesium stearate was added and mixed, and the mixture was placed in a rotary tableting machine and was tableted by using a 12-mm punch, giving tablets having a tablet thickness of 6.18 mm.

The formulae of the orally disintegrating tablets of Examples 19 to 24 are shown in Table 13.

TABLE 13

(Unit: mg)

| | | | Example 19 | Example 20 | Example 21 | Example 22 | Example 23 | Example 24 |
|---|---|---|---|---|---|---|---|---|
| Masking particle | Core particle | Sitagliptin phosphate | 124.1 | 124.1 | 124.1 | 124.1 | 124.1 | 124.1 |
| | | Low-substituted hydroxypropyl cellulose | 7.5 | 7.5 | 7.5 | 7.5 | 7.5 | 7.5 |
| | | Hydroxypropyl cellulose | 17.9 | 17.9 | 17.9 | 17.9 | 17.9 | 17.9 |
| | Separating layer | Talc | 75.3 | 75.3 | 75.3 | 75.3 | 75.3 | 75.3 |
| | | Hydroxypropyl cellulose | 29 | 29 | 29 | 29 | 29 | 29 |
| | Interlayer | Sodium hydrogen carbonate | 29.7 | 29.7 | 29.7 | 0 | 0 | 0 |
| | | Sodium carbonate | 0 | 0 | 0 | 29.7 | 29.7 | 29.7 |
| | | Talc | 16 | 16 | 16 | 16 | 16 | 16 |
| | | Hydroxypropyl cellulose | 8 | 8 | 8 | 8 | 8 | 8 |
| | Masking layer | Aminoalkyl methacrylate copolymer E | 21.3 | 27.4 | 33.5 | 21.3 | 27.4 | 33.5 |
| | | Talc | 21.3 | 27.4 | 33.5 | 21.3 | 27.4 | 33.5 |
| | Subtotal | | 350.1 | 362.3 | 374.5 | 350.1 | 362.3 | 374.5 |
| Tablet | Excipients mixture | Rapidly disintegrating granule | 365 | 365 | 365 | 365 | 365 | 365 |
| | | Light anhydrous silicic acid | 7.6 | 7.6 | 7.6 | 7.6 | 7.6 | 7.6 |
| | | Aspartame | 30 | 30 | 30 | 30 | 30 | 30 |
| | | Magnesium stearate | 3.1 | 3.1 | 3.1 | 3.1 | 3.1 | 3.1 |
| | Subtotal | | 405.7 | 405.7 | 405.7 | 405.7 | 405.7 | 405.7 |
| | Total | | 755.8 | 768 | 780.2 | 755.8 | 768 | 780.2 |

Figure 10:
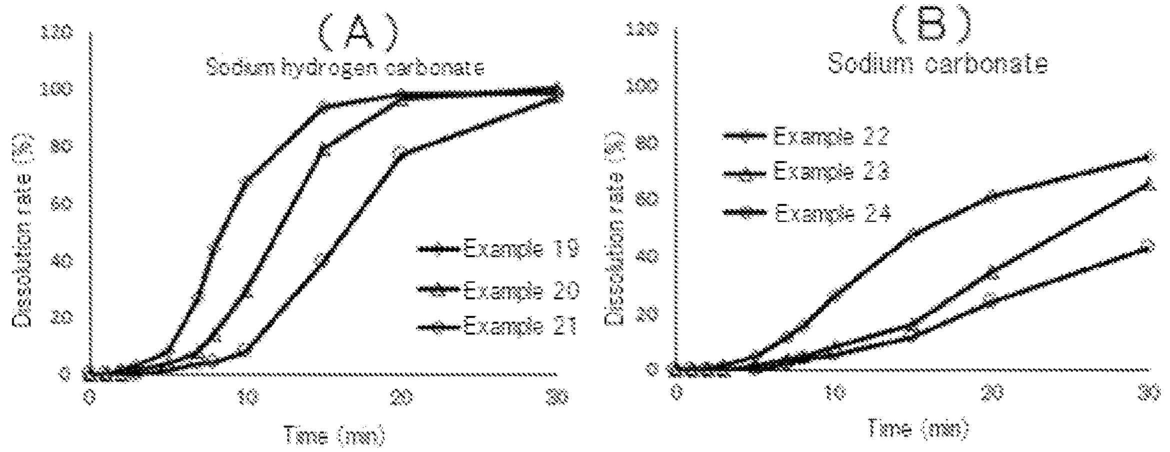
FIG. 10 are graphs showing the dissolution test results of sitagliptin phosphate from orally disintegrating tablets of Examples 19 to 24.

The orally disintegrating tablets of Examples 19 to 24 were subjected to the dissolution test. Changes in dissolution rate of sitagliptin phosphate are shown in FIG. 10.

As shown in FIG. 10(A), the tablets of Examples 19 to 21, which contained sodium hydrogen carbonate as the carbonate, had lag times of 1.7 minutes, 2.8 minutes, and 4.3 minutes and rapid drug release rates of 17.0%/min, 10.0%/min, and 6.3%/min, respectively.

In contrast, as shown in FIG. 10(B), the tablets of Examples 22 to 24, which contained sodium carbonate as the carbonate, had sufficient lag Limes of 2.5 minutes, 4.1 minutes, and 6.1 minutes, respectively, but had insufficient drug release rates of 4.3%/min, 3.7%/min, and 1.9%/min, respectively, and failed to achieve 100% elution even 30 minutes after the start of the test.

Figure 11:
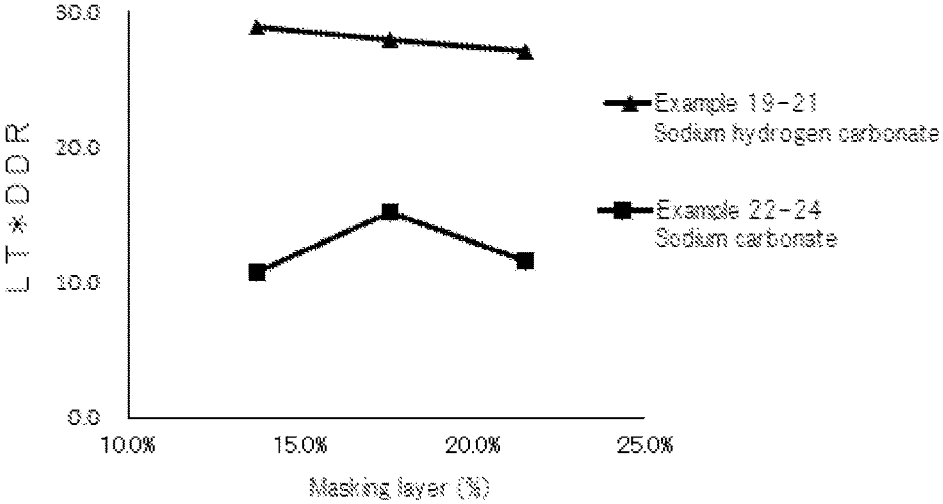
FIG. 11 is a graph comparing products of lag times and drug release rates (LT*DRR) between orally disintegrating tablets of Examples 19 to 21 in which sodium hydrogen carbonate was used as the carbonate and orally disintegrating tablets of Examples 22 to 24 in which sodium carbonate was used as the carbonate.

To compare the timed-elution masking performance of different carbonates, the products of lag times and drug release rates (LT*DRR) were compared between Examples 19 to 21 and Examples 22 to 24. The results are shown in Table 14 and FIG. 11. In FIG. 11, the horizontal axis is the ratio of the mass of the masking layer to the mass of the drug-containing particles, and the vertical axis is the product of the lag time and the drug release rate (LT*DRR).

It is preferable that timed-elution masking particles and pharmaceutical compositions containing the timed-elution masking particles have a long lag time and a high drug release rate, and thus a larger LT*DRR value indicates higher performance.

TABLE 14

| | Example 19 | Example 20 | Example 21 | Example 22 | Example 23 | Example 24 |
|---|---|---|---|---|---|---|
| Lag time(LT)(min) | 1.7 | 2.8 | 4.3 | 2.5 | 4.1 | 6.1 |
| Drug release rate(DRR)(%/min) | 17.0 | 10.0 | 6.3 | 4.3 | 3.7 | 1.9 |
| LT*DRR | 28.9 | 28.0 | 27.1 | 10.8 | 15.2 | 11.6 |

As shown in Table 14 and FIG. 11, at any masking ratio, the tablets of Examples 19 to 21 had larger LT*DRR values than those of Examples 22 to 24. This reveals that sodium hydrogen carbonate is better than sodium carbonate as the carbonate used in the masking particles of the present invention and in pharmaceutical compositions containing the masking particles. The orally disintegrating tablets of Examples 22 to 24, however, had sufficient lag times and drug release rates to be practically usable as the orally disintegrating tablet.

Figure 12:
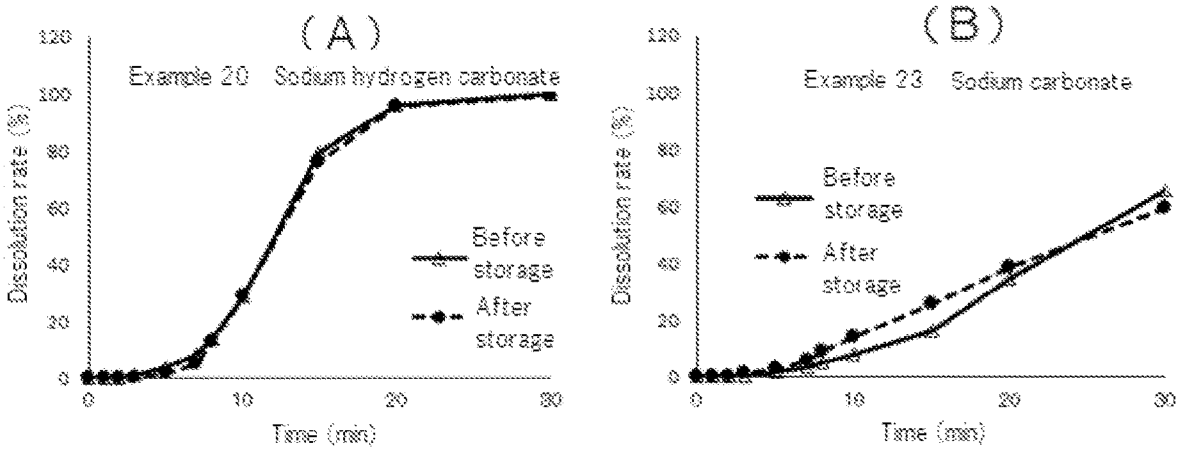
FIG. 12 are graphs comparing the dissolution test results of sitagliptin phosphate from orally disintegrating tablets before and after storage in which the orally disintegrating tablets of each of Example 20 and Example 23 were stored in a humid condition at 25° C. and 75% RH for two weeks.

Next, the orally disintegrating tablets of Example 20 and Example 23 were stored in a humid condition (25° C., 75% RH) for two weeks, and dissolution test was performed before and after the storage. Changes in dissolution rate of sitagliptin phosphate are shown in FIG. 12. The lag times, the drug release rates, and the LT*DRR values are shown in Table 15.

TABLE 15

| | Example 20 | | Example 23 | |
|---|---|---|---|---|
| | Before storage | After storage | Before storage | After storage |
| Lag time(LT)(min) | 2.8 | 4.2 | 4.1 | 2.8 |
| Drug release rate(DRR)(%/min) | 10.0 | 9.3 | 3.7 | 2.5 |
| LT*DRR | 28.0 | 39.1 | 15.2 | 7.0 |

The orally disintegrating tablets of Example 20, which contained sodium hydrogen carbonate as the carbonate, had a longer lag time after the storage in the humid condition, but the drug release rate was not greatly changed. Accordingly, the product of the lag time and the drug release rate (LT*DRR) increased.

In contrast, the orally disintegrating tablets of Example 23, which contained sodium carbonate as the carbonate, had a shorter lag time and a lower drug release rate after the storage in the humid condition. Accordingly, the product of the lag time and the drug release rate (LT*DRR) decreased. The reduction in LT*DRR of the orally disintegrating tablets of Example 23 by storage was acceptable for practical use.

Using sodium hydrogen carbonate as the carbonate was found to give better storage stability.

(3) Evaluation of Drug Dissolution from Masking Particles According to Patent Literature 1

Masking particles that comprise a core particle containing sitagliptin phosphate and an interlayer containing, instead of sodium hydrogen carbonate, trisodium citrate dihydrate as a salting out-type insolubilizer and hypromellose as a substance to be insolubilized in a salting out-type manner used in Example 4 in Patent Literature 1 (JP 4277904 B) were produced by the following procedures.

Reference Examples 2 and 3

Preparation of Core Particles

In an agitation mixing granulator, 249.1 g of sitagliptin phosphate, 15.1 g of low-substituted hydroxypropyl cellulose, and 35.9 g of hydroxypropyl cellulose were placed and mixed. While the whole was stirred, a mixed liquid of 21 g of ethanol and 21 g of purified water was then sprayed, and the whole was granulated. The product was sieved, and particles passed through a 60-mesh (250 μm) sieve but not passed through a 140-mesh (106 μm) sieve were collected as core particles.

Preparation of Separating Layer-Coated Particles

In a tumbling fluidized-bed coating machine, 179.4 g of the core particles were placed, and the coating liquid (1) was sprayed to give separating layer-coated particles.

Preparation of Coating Liquid (19)

To a solution of 9.7 g of hypromellose (manufactured by Shin-Etsu Chemical; TC5E, hereinafter the same applies) in 400.6 g purified water, 17.1 g of talc and 27.1 g of pulverized trisodium citrate dihydrate (manufactured by FUJIFILM Wako Pure Chemical Corporation, hereinafter the same applies) were added, and the whole was stirred to give a coating liquid (19).

Preparation of Drug-Containing Particles

In a tumbling fluidized-bed coating machine, 200 g of the separating layer-coated particles were placed, and the coating liquid (19) was sprayed to give drug-containing particles.

Preparation of Masking Particles

In a tumbling fluidized-bed coating machine, 221.3 g of the drug-containing particles were placed, and the coating liquid (3) was sprayed to give masking layer-coated particles.

Particles having the masking layer at a mass ratio of 5% relative to the mass of the drug-containing particles were regarded as Reference Example 2; and particles having the masking layer at a mass ratio of 10% were regarded as Reference Example 3.

Reference Example 1

A similar procedure to that for Reference Examples 2 and 3 was performed to prepare drug-containing particles as Reference Example 1.

The formulae of the masking particles of Reference Examples 1 to 3 are shown in Table 16.

TABLE 16

(Unit: mg)

| | Ingredient | Reference Example 1 | Reference Example 2 | Reference Example 3 |
|---|---|---|---|---|
| Core particle | Sitagliptin phosphate | 124.1 | 124.1 | 124.1 |
| | Low-substituted hydroxypropyl cellulose | 7.5 | 7.5 | 7.5 |
| | Hydroxypropyl cellulose | 17.9 | 17.9 | 17.9 |
| Separating layer | Talo | 34.3 | 34.3 | 34.3 |
| | Hydroxypropyl cellulose | 13.2 | 13.2 | 13.2 |
| Interlayer | Trisodium citrate dihydrate | 26.7 | 26.7 | 26.7 |
| | Talc | 16.8 | 16.8 | 16.8 |
| | Hydroxypropyl cellulose | 9.6 | 9.6 | 9.6 |
| Masking layer | Aminoalkyl methacrylate copolymer E | 0 | 6.3 | 12.5 |
| | Talc | 0 | 6.3 | 12.5 |
| Total | | 250.1 | 262.7 | 275.1 |

(Evaluation Results)

Figure 13:
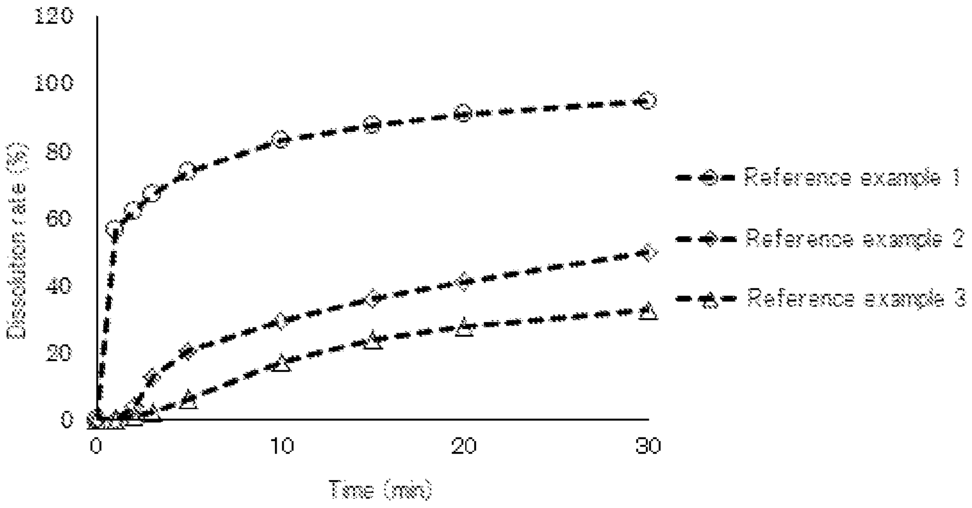
FIG. 13 is a graph showing the dissolution test results of sitagliptin phosphate from masking particles according to Patent Literature 1 (JP 4277904 B).

The particles of Reference Examples 1 to 3 were subjected to the dissolution test. Changes in dissolution rate of sitagliptin phosphate are shown in FIG. 13.

The particles of Reference Example 1 had no lag time and rapidly released the drug. The particles of Reference Examples 2 and 3 had short lag times of 1.2 minutes and 1.7 minutes, respectively. The particles had low drug release rates of 1.2%/min and 0.5%/min, respectively, and eluted only 50% and 32.6% of the drug, respectively, 30 minutes after the start of the dissolution test.

The results suggest that the dissolution control mechanism taught by Patent Literature 1 (JP 4277904 B) suppresses the drug bitterness in the mouth, but achieves insufficient drug dissolution, and is thought to achieve insufficient drug absorption from the digestive tract.

INDUSTRIAL APPLICABILITY

The masking particles of the present invention do not release a drug of a salt with an acid in the mouth after taking, are unlikely to give the taste of a contained drug even having an unpleasant taste, and suppress drug absorption from the oral cavity or pharynx. After swallowing, the masking particles rapidly release a drug, and thus the drug is sufficiently absorbed from the digestive tract. The release suppression time of the drug of a salt with an acid can be accurately controlled to an intended time, and thus an appropriate preparation can be produced depending on the type of drug or the dosage form.

The invention claimed is:

1. Masking particles comprising a drug-containing particle containing a drug of a salt with an acid and containing sodium hydrogen carbonate, the drug-containing particle being coated with a coating layer containing a water-insoluble polymer.

2. The masking particles according to claim 1, wherein the sodium hydrogen carbonate is contained in an amount of 0.1 to 50% by weight relative to a total amount of the drug-containing particles.

3. The masking particles according to claim 1, wherein the sodium hydrogen carbonate is contained in an amount of 0.001 to 10 parts by weight relative to 1 part by weight of the drug of a salt with an acid.

4. The masking particles according to claim 1, wherein a content of the coating layer is 0.01 to 1 part by weight relative to 1 part by weight of the drug-containing particles.

5. The masking particles according to claim 1, wherein the drug-containing particle is a uniform particle containing the drug of a salt with an acid and containing the sodium hydrogen carbonate.

6. The masking particles according to claim 1, wherein the drug-containing particle comprises a portion containing the drug of a salt with an acid and a separate portion containing the sodium hydrogen carbonate.

7. The masking particles according to claim 6, wherein the drug-containing particle comprises a core particle and an interlayer on the core particle, and the core particle contains the drug of a salt with an acid, and the interlayer contains the sodium hydrogen carbonate, or the core particle contains the sodium hydrogen carbonate, and the interlayer contains the drug of a salt with an acid.

8. The masking particles according to claim 7, further comprising a separating layer between the core particle and the interlayer of the drug-containing particle.

9. The masking particles according to claim 7, wherein the core particle contains a disintegrant.

10. The masking particles according to claim 7, wherein the interlayer or the interlayer and the separating layer contain a binder and/or a fluidizer or lubricant.

11. A tablet, a capsule, granules, fine granules, or a powder comprising the masking particles according to claim 1.

12. An orally disintegrating tablet comprising the masking particles according to claim 1.

13. A method of producing masking particles, the method comprising a step of coating a drug-containing particle containing a drug of a salt with an acid and containing sodium hydrogen carbonate with a coating layer containing a water-insoluble polymer.

14. A method of controlling dissolution or release of a drug of a salt with an acid from particles containing the drug, the method comprising coating a drug-containing particle containing the drug of a salt with an acid and containing sodium hydrogen carbonate with a coating layer containing a water-insoluble polymer.

* * * * *